United States Patent
Wiener et al.

(10) Patent No.: US 11,387,004 B2
(45) Date of Patent: Jul. 12, 2022

(54) STANDING DESK MAT

(71) Applicant: Thermogenesis Group, Inc., Bellevue, WA (US)

(72) Inventors: Ron Wiener, Mercer Island, WA (US); Andrew Rosenbaum, Mercer Island, WA (US)

(73) Assignee: Thermogenesis Group, Inc., Bellevue, WA (US)

( * ) Notice: Subject to any disclaimer, the term of this patent is extended or adjusted under 35 U.S.C. 154(b) by 54 days.

(21) Appl. No.: 17/096,360

(22) Filed: Nov. 12, 2020

(65) Prior Publication Data

US 2021/0065916 A1    Mar. 4, 2021

Related U.S. Application Data

(63) Continuation-in-part of application No. 15/921,846, filed on Mar. 15, 2018, now Pat. No. 11,116,343.

(51) Int. Cl.
*G16H 50/80*    (2018.01)
*A47G 27/02*    (2006.01)

(52) U.S. Cl.
CPC ............ *G16H 50/80* (2018.01); *A47G 27/02* (2013.01); *A47G 2200/226* (2013.01)

(58) Field of Classification Search
CPC .. G16H 50/80; A47G 27/02; A47G 2200/226; A47G 27/0231
USPC .................................................... 73/862.041
See application file for complete search history.

(56) References Cited

U.S. PATENT DOCUMENTS

| | | |
|---|---|---|
| 5,285,022 A | 2/1994 | Antone |
| 5,388,591 A | 2/1995 | De Luca et al. |
| 6,063,046 A | 5/2000 | Allum |
| 6,085,697 A | 7/2000 | Fuchs |
| 6,119,530 A | 9/2000 | Oddsson et al. |
| 6,870,477 B2 | 3/2005 | Gruteser et al. |
| 7,381,152 B2 | 6/2008 | Couvilion, Jr. et al. |
| 7,900,523 B2 | 3/2011 | Kogure et al. |
| 7,938,751 B2 | 5/2011 | Nicolas et al. |
| 8,339,371 B2 | 12/2012 | Soto et al. |

(Continued)

FOREIGN PATENT DOCUMENTS

| | | | |
|---|---|---|---|
| TW | M599451 U | * 8/2020 | |
| WO | WO-2021258101 A1 | * 12/2021 | ......... G06K 9/00718 |

OTHER PUBLICATIONS

Official Action for U.S. Appl. No. 15/921,846, dated Dec. 27, 2019 20 pages.

(Continued)

*Primary Examiner* — Octavia Hollington
(74) *Attorney, Agent, or Firm* — Sheridan Ross PC

(57) ABSTRACT

Standing desks, such as fixed work surfaces or height-adjustable desks or computer/workstation supports, provide relief from computer or other desk work that might otherwise force a user to remain seated. However, concerns about utilization and comfort are points of resistance to standing desks. A "smart" pressure sensing mat is provided that may provide additional cushioning and comfort as well as a source of data input for record keeping, usage verification, user identification, and control signals. Identification of users' utilizing a mat may then be utilized for contact-tracing to identify possible exposure or transmission of contagions in a workplace.

20 Claims, 14 Drawing Sheets

(56) References Cited

U.S. PATENT DOCUMENTS

| | | |
|---|---|---|
| 8,613,678 B2 | 12/2013 | Nusbaum et al. |
| 8,675,018 B2 | 3/2014 | Mishra et al. |
| 8,810,424 B2 | 8/2014 | Garcia |
| 9,212,814 B2 | 12/2015 | Puljan |
| 9,485,839 B2 | 11/2016 | Kiser |
| 9,486,070 B2 | 11/2016 | Labrosse et al. |
| 9,949,640 B2 | 4/2018 | Horseman |
| 10,021,530 B2 | 7/2018 | Sigal et al. |
| 10,477,355 B1 | 11/2019 | Niranjayan et al. |
| 10,496,155 B2 | 12/2019 | Schwarz et al. |
| 10,801,166 B2 | 10/2020 | Trilling et al. |
| 11,013,472 B1* | 5/2021 | Frieder ............. H04W 52/0254 |
| 2006/0152378 A1 | 7/2006 | Lokhorst et al. |
| 2009/0186698 A1 | 7/2009 | Ludden |
| 2011/0132276 A1 | 6/2011 | Lanny |
| 2011/0245732 A1 | 10/2011 | Mravyan et al. |
| 2012/0053424 A1* | 3/2012 | Kenalty ............... A61B 5/6892 600/300 |
| 2012/0253233 A1 | 10/2012 | Greene et al. |
| 2012/0309531 A1 | 12/2012 | Gong et al. |
| 2013/0116852 A1 | 5/2013 | Dijk et al. |
| 2014/0195023 A1 | 7/2014 | Statham et al. |
| 2016/0242719 A1 | 8/2016 | Yorkston et al. |
| 2016/0374618 A1 | 12/2016 | Giovangrandi |
| 2017/0028258 A1 | 2/2017 | Liu et al. |
| 2017/0089775 A1 | 3/2017 | Hsu et al. |
| 2017/0177833 A1 | 6/2017 | Lewallen et al. |
| 2017/0196195 A1 | 7/2017 | Wisdom |
| 2018/0125413 A1 | 5/2018 | Smith, Jr. et al. |
| 2019/0090816 A1* | 3/2019 | Horseman ............ A61B 5/0537 |
| 2019/0282012 A1 | 9/2019 | Wiener et al. |
| 2019/0285389 A1 | 9/2019 | Alexandre et al. |
| 2020/0394367 A1 | 12/2020 | Fleetwod et al. |
| 2021/0319912 A1* | 10/2021 | Bandy ..................... G01S 15/08 |
| 2021/0366071 A1* | 11/2021 | Hager .................... G06Q 50/01 |
| 2021/0374891 A1* | 12/2021 | Menon .................. G16H 50/80 |

OTHER PUBLICATIONS

Official Action for U.S. Appl. No. 15/921,846, dated Feb. 25, 2019 16 pages.

Official Action for U.S. Appl. No. 15/921,846, dated Jun. 26, 2020 23 pages.

Official Action for U.S. Appl. No. 15/921,846, dated Sep. 5, 2019 22 pages.

Official Action for U.S. Appl. No. 15/921,846, dated Feb. 8, 2021 21 pages.

Notice of Allowance for U.S. Appl. No. 15/921,846, dated May 26, 2021 10 pages.

\* cited by examiner

STANDING DESK MAT

CROSS-REFERENCE TO RELATED APPLICATIONS

The present application is a continuation-in-part and claims the benefit of U.S. patent application Ser. No. 15/921,846, filed on Mar. 15, 2018, and is incorporated herein by reference in its entirety.

FIELD OF THE DISCLOSURE

The present disclosure is generally directed toward sensing electronics and related systems.

BACKGROUND

A significant upheaval in daily life, including work life, occurred when COVID-19 reached pandemic levels. Reducing person-to-person interactions became paramount in order to reduce the rate of transmission. Workers, such as office workers, who could work from home did so to the extent possible; open floorplan offices were depopulated or emptied entirely. Workers with private offices were able to work while maintaining the prescribed social-distance practices, at least while within their office. Ideally, each worker is provided with a dedicated, single-user, private office. However, such an investment in time, money, and floorspace is beyond the ability of many employers.

A consequence of workers that work from home more often, is that dedicated, single-user offices and workspaces are more frequently left empty. Even employers who can provide dedicated offices may be reluctant to do so if a substantial portion of the workforce is working from home. As a result, office spaces are becoming more physically separate (e.g., increased workspace-to-workspace distances, isolated air handling, barriers, etc.), but rather than being dedicated for the sole use of one worker, are shared between a pool of workers. Such measures seek to balance resource utilization with the need to decrease the number physical exposures between the workers, as well as making contagion transmission less likely. Even with such measures, it remains a non-zero possibility that a worker, or other person, will be at a worksite while infected and expose other workers to a contagion.

Pressure mats are known systems whereby a component is provided in a deformable body to indicate occupancy or a lack of occupancy. Pressure mats are often utilized in situations where safety is an issue, such as to ensure a worker is standing in a designated location before a machine is enabled to operate. Alternatively, pressure mats are utilized to trigger door openers or other equipment upon detection of an occupant.

The use of standing desks continues to increase in popularity. Many organizations utilize wellness managers to promote the health and safety of their workers, which more and more frequently includes the use of standing desks. Wellness managers may have to decide whether purchasing standing desks, or selecting other option, would provide the greatest benefit. For example, wellness managers may know that company-provided gym memberships have a particular utilization rate. Similarly, if sit-stand desks were to be provided to workers, how often and for what duration would they be used in the standing configuration? Without being able to answer that question, wellness managers may select one of the other options and deny their workers the opportunity to improve their wellbeing while they work.

Workers, such as in a pilot program, could be asked about their utilization. However, workers may forget or resist additional reporting tasks or, if reported, may or may not accurately report their use. Similarly, a pressure mat may be able to determine that something is on the mat associated with a particular location, however pressure mats may report occupancy when the occupant is a box or leg of a chair.

SUMMARY

Wellness managers and other personnel responsible for making wellness purchasing decisions may be reluctant to purchase standing desks or sit-stand desks due to a lack of verifiable usage data. In contrast, gym membership utilization can be determined by monitoring equipment use, badge scans, or other well-known means. However, gyms may be intimidating, or their use postponed until "when I have the time," for many workers. Being able to spend at least a few minutes standing at work may provide benefits to many workers who may otherwise not take advantage of other wellness opportunities or to supplement the activities that they do utilize. As insurance companies, wellness managers, and others incentivize healthful activities, some may be tempted to game the system. For example, a company owned gym may require badge-scans as a means to monitor participation in wellness activities, such as exercising at the gym, but some may be tempted to scan their badge and leave without performing any exercises. Standing versus sitting may be incentivized, however, self-reporting time spent standing may not be an accurate representation of actual time spent standing. A pressure mat may be able to determine that something is on a mat, but if that "something" is a person standing, a wheel of a chair, or a box, requires more than a pressure mat.

It is with respect to the above issues and other problems that the embodiments presented herein were contemplated.

As an overview, and in one embodiment, a pressure sensing mat (or, more simply, "mat") is provided. The mat provides data as received from pressure sensing or other sensing components to report data to and/or trigger other systems in response to a particular use. The mat preferably provides comfort and otherwise promotes use, such as for standing upon while a user is at a standing desk or utilizing a sit-stand desk in a standing configuration.

In one embodiment, a system is disclosed, comprising: a pressure sensing mat comprising a plurality of sensing portions; a processor; a component configured to communicate with the processor; and wherein the pressure sensing portions provide signals to the processor in accord with a received pressure and location of the pressure on the pressure sensing mat; wherein the processor receives the signals from the plurality of pressure sensing components and further determines an indicia of use and output the indicia of use to the component and wherein the indicia of use comprises an indication of whether the pressure sensing mat is being used by a user that is standing on the pressure sensing mat; and the component provides a first response, when the indicia of use indicates the user is standing and a second response, when the indicia of use does not indicate standing.

In another embodiment, a pressure sensing mat is disclosed, comprising: a communication interface to a network; a supporting structure; a pressure sensing component supported by the supporting structure and configured to provide signals in accord with a received pressure and location of the pressure on the pressure sensing mat; a processor to receive the signals from the pressure sensing component and determine an indicia of use, from the signals, and output the indicia of use via the communication interface; and wherein the indicia of use comprises an indication of whether the pressure sensing mat is being used by a user that is standing on the pressure sensing mat.

In another embodiment, a method is disclosed, comprising: detecting pressure on a pressure sensing mat; analyzing signals from portions of the pressure sensing mat; outputting, from the pressure sensing mat, indicia of use associated with standing use, upon the analyzed signals indicating the pressure sensing mat is being utilized by a standing user, and non-standing use, upon the analyzed signals indicating the pressure sensing mat is not being utilized by a user while standing; and reporting the indicia to a component.

The phrases "at least one," "one or more," and "and/or" are open-ended expressions that are both conjunctive and disjunctive in operation. For example, each of the expressions "at least one of A, B, and C," "at least one of A, B, or C," "one or more of A, B, and C," "one or more of A, B, or C," and "A, B, and/or C" means A alone, B alone, C alone, A and B together, A and C together, B and C together, or A, B, and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The term "computer-readable medium," as used herein, refers to any tangible storage that participates in providing instructions to a processor for execution. Such a medium may take many forms, including, but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, an EPROM, a FLASH-EPROM, a solid-state medium like a memory card, any other memory chip or cartridge, or any other medium from which a computer can read. When the computer-readable media is configured as a database, it is to be understood that the database may be any type of database, such as relational, hierarchical, object-oriented, and/or the like. Accordingly, the disclosure is considered to include a tangible storage medium and prior art-recognized equivalents and successor media, in which the software implementations of the present disclosure are stored.

While machine-executable instructions may be stored and executed locally to a particular machine (e.g., personal computer, mobile computing device, laptop, etc.), it should be appreciated that the storage of data and/or instructions and/or the execution of at least a portion of the instructions may be provided via connectivity to a remote data storage and/or processing device or collection of devices, commonly known to as "the cloud," but may include a public, private, dedicated, shared and/or other service bureau, computing service, and/or "server farm."

The terms "determine," "calculate," and "compute," and variations thereof, as used herein, are used interchangeably and include any type of methodology, process, mathematical operation, or technique.

The term "module," as used herein, refers to any known or later-developed hardware, software, firmware, artificial intelligence, fuzzy logic, or combination of hardware and software that is capable of performing the functionality associated with that element. Also, while the disclosure is described in terms of exemplary embodiments, it should be appreciated that other aspects of the disclosure can be separately claimed.

BRIEF DESCRIPTION OF THE DRAWINGS

The present disclosure is described in conjunction with the appended figures.

DETAILED DESCRIPTION

The ensuing description provides embodiments only and is not intended to limit the scope, applicability, or configuration of the claims. Rather, the ensuing description will provide those skilled in the art with an enabling description for implementing the embodiments. It will be understood that various changes may be made in the function and arrangement of elements without departing from the spirit and scope of the appended claims.

Any reference in the description comprising an element number, without a subelement identifier when a subelement identifier exists in the figures, when used in the plural, is intended to reference any two or more elements with a like element number. When such a reference is made in the singular form, it is intended to reference one of the elements with the like element number without limitation to a specific one of the elements. Any explicit usage herein to the contrary or providing further qualification or identification shall take precedence.

The exemplary systems and methods of this disclosure will also be described in relation to analysis software, modules, and associated analysis hardware. However, to avoid unnecessarily obscuring the present disclosure, the following description omits well-known structures, components, and devices, which may be omitted from or shown in a simplified form in the figures or otherwise summarized.

For purposes of explanation, numerous details are set forth in order to provide a thorough understanding of the present disclosure. It should be appreciated, however, that the present disclosure may be practiced in a variety of ways beyond the specific details set forth herein.

Figure 1:
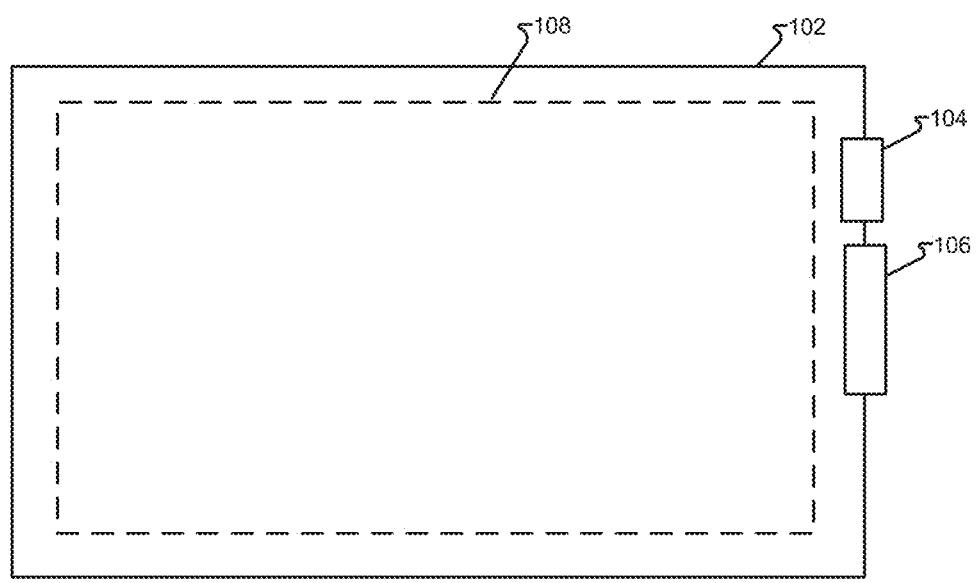
FIG. 1 depicts a mat in accordance with embodiments of the present disclosure.

FIG. 1 depicts mat 102 in accordance with embodiments of the present disclosure. In one embodiment, mat 102 comprises pressure sensing area 108. Mat 102 may provide cushioning, ridges, or other physical features to promote comfort and use. Pressure sensing area 108 comprises a plurality of pressure sensing components and/or pressure sensing areas and may utilize communication interface 106 to send and/or receive data to other components, which will be described in greater detail with respect to the embodiments below. In another embodiment, power control component 104 receives electrical power from an electrical plug to a power source and/or battery (not shown). Power control component 104 may comprise a switch to selectively activate/deactivate power consuming components of mat 102. Power control component 104 may be omitted when electrical power is provided by communication interface 106 (e.g., power-over-ethernet, USB, etc.).

In another embodiment communication interface 106 comprises a communication interface for wired and/or wireless communications to other components (e.g., Wi-Fi, Bluetooth, ethernet, USB, near field communications, etc.). Although mat 102 is depicted as rectangular in shape, it should be appreciated that other geometries may be utilized without departing from the scope of the disclosure herein.

In another embodiment, mat 102 may perform, at least in part, operations similar to those of a touch pad. For example, a user may provide inputs in the form of a particular gesture, tapping pattern, or touch a particular location within pressure sensing area 108. Mat 102 may then provide the signals, such as raw signals (e.g., voltage or other reported value from one or more pressure sensing components) and/or a signal providing a determined meaning (e.g., vacant, occupied, standing user, occupied by non-standing user, etc.), to another component. Such signals may indicate distress, comprise an authentication, or initiate a particular operation. For example, a user at a bank may have a particular tapping pattern that indicates distress to alert security personnel, a user may be authorized to omit a conventional password or utilize a simplified password if they perform a certain gesture, such as perform two taps on the left portion of mat 102 and then a sweeping motion to the upper right corner, as a means of authentication. As will be described in more detail with respect to certain embodiments that follow, mat 102 may be utilized with a powered or unpowered sit-stand desk or computer workstation support. Accordingly, tapping a particular "hotspot" of mat 102 or performing a pre-determined gesture may trigger a powered sit-stand desk or support to transition from seated use to standing use or vice versa. Optionally, mat 102 may incorporate one or more of heat, massage, ventilation, haptic feedback, sound, lights, or other input, output, or usability features.

Figure 2:
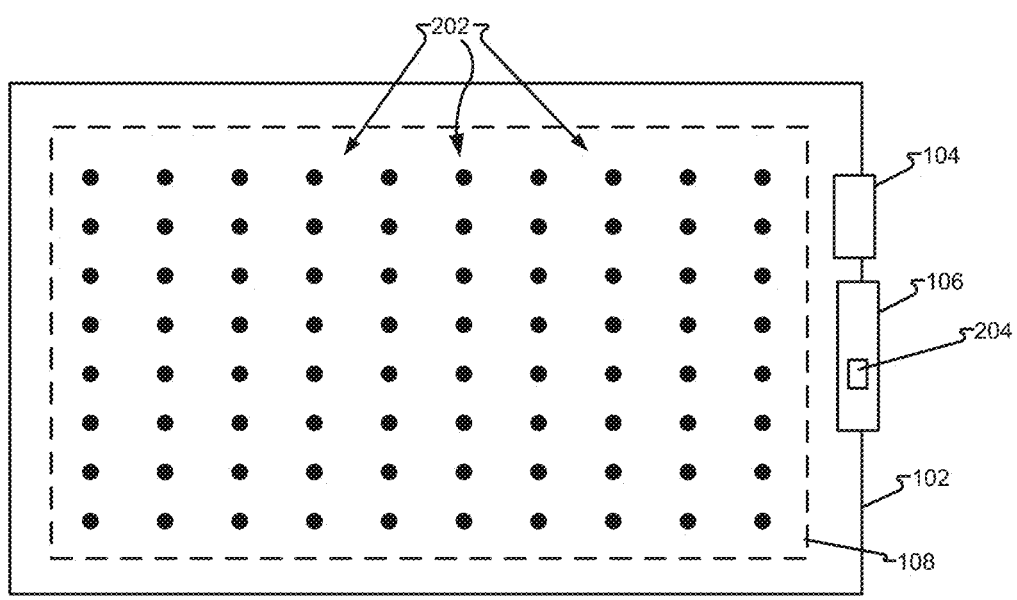
FIG. 2 depicts the mat comprising a first configuration of sensing components in accordance with embodiments of the present disclosure.

FIG. 2 depicts mat 102 comprising a configuration of sensing components 202 in accordance with embodiments of the present disclosure. In one embodiment, sensing components 202 are uniformly provided within pressure sensing area 108. Each of sensing components 202 provides an output which may be further provided as a raw signal from each component via communication interface 106 and/or aggregated or otherwise processed via processor 204 performing operations to combine, modify, aggregate, or otherwise process the data from one or more of sensing components 202. In another embodiment, communication interface 106 comprises an output, such as a speaker, LED, haptic, etc. such as may be perceived by a user. In a further embodiment, communication interface 106 may comprise processor 204 performing operations that translates signals received upon ones of sensing components 202 as commands. For example, a particular tapping pattern or a particular gesture traced out by a user's foot within pressure sensing area 108 may be interpreted as a command input. In another embodiment, processor 204 may detect a failure of one or more of sensing components 202. For example, one of sensing components 202 may be "stuck" and continuously report a particular pressure. Processor 204 may exclude data from the stuck one of sensing components 202 or provide an alternative value in place of the "stuck" data value, such as duplicating a value of a neighboring one of sensing components 202 or an average or extrapolated value of a plurality of neighboring ones of sensing components 202.

Sensing components 202 are variously embodied. Sensing components 202 may provide a heterogeneous or homogenous collection of types and/or sensitivities for ones of sensing components 202. Sensing components 202 may comprise pressure sensing (e.g., pneumatic, piezoelectric, etc.), presence (e.g., capacitive, inductive, etc.), and/or obscured (e.g., photosensor, photo transducer. etc.). However, while utilization of sensing components 202 that comprise detecting whether or not ones of sensing components 202 are obscured may be utilized, at least in part, the embodiments herein, unless otherwise specified, are directed to sensing components 202 that provide an output indicating a pressure level, amount, or indicia to a processor, such as processor 204, or to a processor of a component in communication with mat 102 via communication interface 106.

In another embodiment, mat 102 may be utilized with one or more discrete components to provide additional or alternative physical properties. For example, mat 102 may provide substantially no padding and be attached to a padding component. In another example, mat 102 may be place on top of or underneath a carpet, rug, ridged pad, etc. Accordingly, mat 102 may incorporate a calibration operation. Processor 204 and/or another processor or computing system in communication with mat 102 via communication interface 106 may prompt a user to perform calibration actions (e.g., step on, step off, etc.) and thereby associate signals produced by sensing components 202 with a user or a particular user. Calibration may be prompted periodically or upon sensing an event, such as dissimilar signal from sensing components 202, such as to determine whether mat 102 is being utilized by a different user or if it has been moved and is now being utilized on a different surface (e.g., carpeted floor to wood floor). A user-event may also prompt calibration. Additionally or alternatively, communication interface 106 may comprise a speaker, LED, or other input-output component to prompt a user to perform calibration activities without requiring another component, such as a computer, smart phone, etc., utilizing an application to communicate with mat 102 via communication interface 106.

Figure 3:
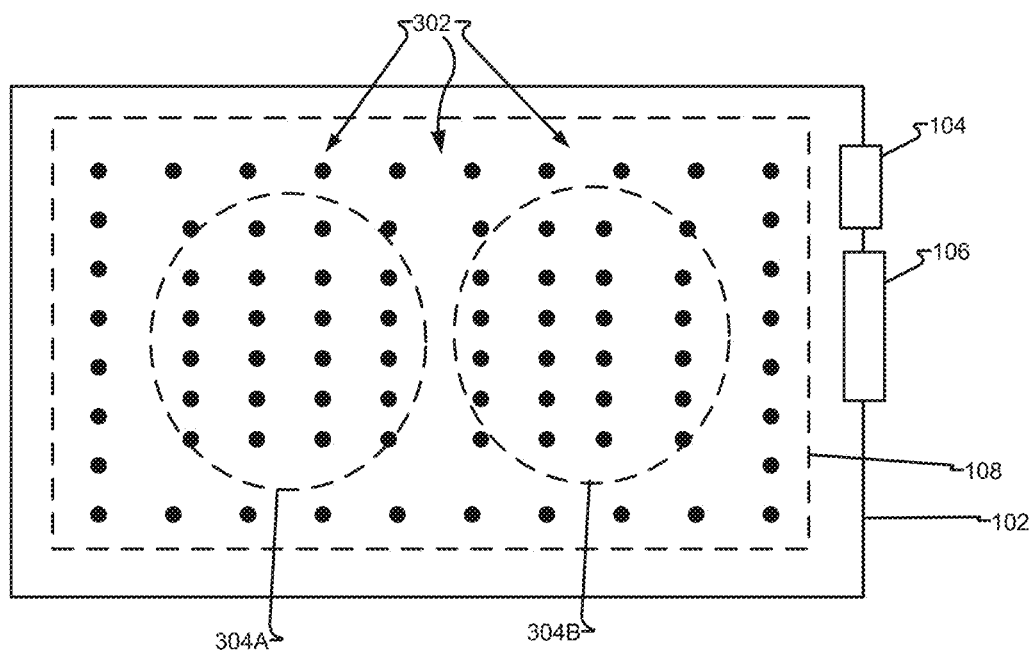
FIG. 3 depicts the mat comprising a second configuration of sensing components in accordance with embodiments of the present disclosure.

FIG. 3 depicts mat 102 comprising a configuration of sensing components 302 in accordance with embodiments of the present disclosure. In one embodiment, sensing components 302 are distributed heterogeneously within pressure sensing area 108, such as having a greater concentration within areas 304A-B, such as may be utilized more extensively by a user standing as compared to sensing components 302 outside of areas 304A-B. As a benefit, pressure sensing area 108 may provide a greater resolution associated with usage as without the need to add excessive sensing components 302 within pressure sensing area 108 that see infrequent or irrelevant usage (e.g., usage while a user transitions to or from standing, but not utilized while standing). It should be appreciated that other distributions may be provided for sensing components 302 without departing from the scope of the disclosure provided.

Figure 4:
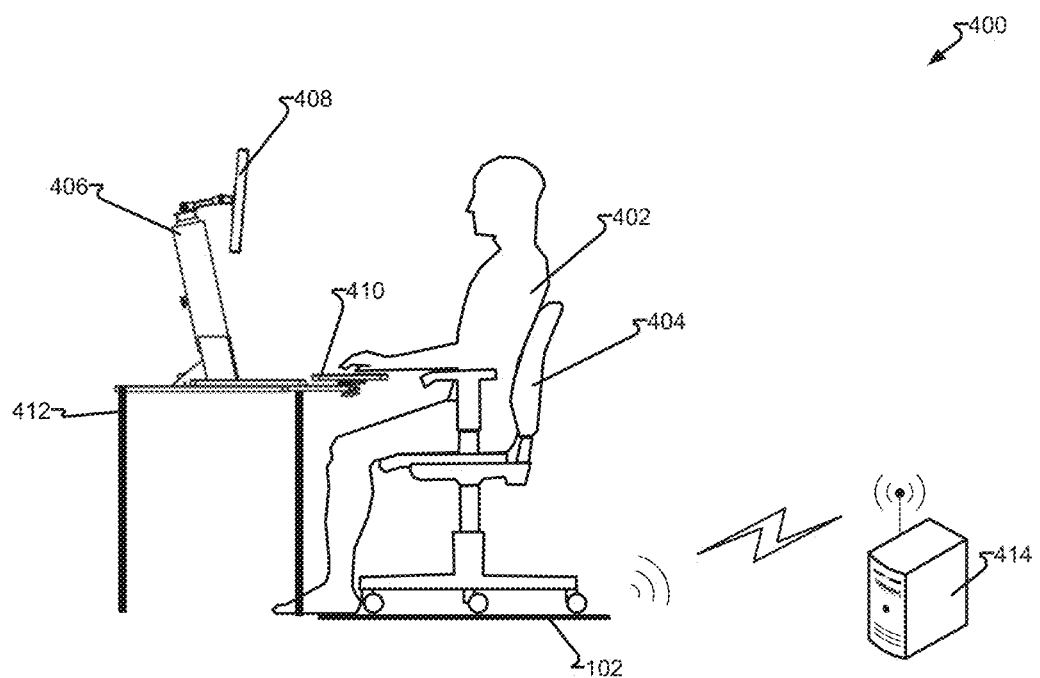
FIG. 4 depicts a first mat usage environment in accordance with embodiments of the present disclosure.

FIG. 4 depicts mat usage environment 400 in accordance with embodiments of the present disclosure. In one embodiment, mat usage environment 400 comprises user 402 seated in chair 404 which is located, partially or entirely, upon mat 102. User 402 is seated, such as to engage sit-stand desk 412, comprising support 406, monitor 408, and devices placed upon keyboard/mouse tray 410. Desk 412 may comprise height-adjusting powered legs to elevate the worksurface of desk 412 or be stationary but comprise a height adjusting structure, such as support 406 and monitor 408 and/or keyboard/mouse tray 410 attached to support 406. Mat 102 may communicate, such as via a wireless connection, to computer 414. Computer 414 may be a dedicated device solely monitoring mat 102 or a collection thereof for an associated collection of users 402. In another embodiment, computer 414 may provide a workstation for user 402 and thereby provide other computing and communication services.

User 402 and chair 404 contacts mat 102 via a number of points. User 402 would have the bulk of their weight distributed across each of the wheels, pads, or legs of chair 404. A trivial portion of weight would be provided by the feet of user 402 or other contact points. Accordingly, computer 414 and/or processor 204 may monitor mat 102 by receiving outputs from sensing components 202, 302.

Figure 5:
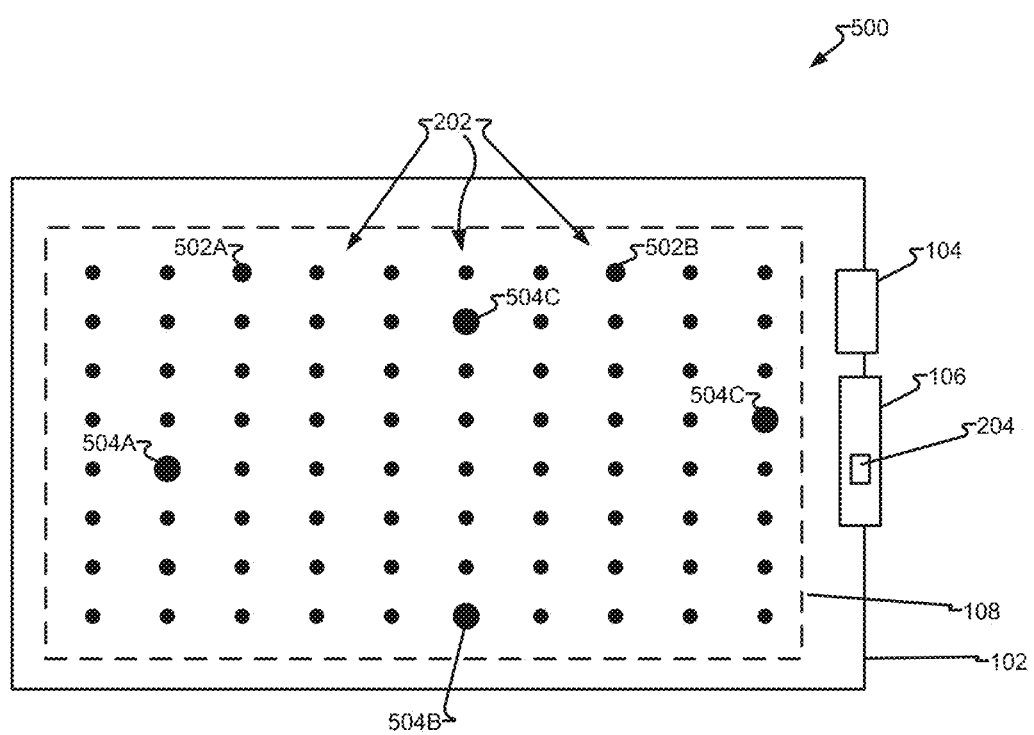
FIG. 5 depicts the mat as used in the first mat usage environment in accordance with embodiments of the present disclosure.

FIG. 5 depicts rendering 500 of mat 102 with sensing components 202 in accordance with embodiments of the present disclosure. In one embodiment, sensing components 202 are depicted as different sizes to indicate dissimilar pressure signal outputs, such as those detected when utilized in mat usage environment 400. For example, chair legs (e.g., contact points of chair 404) on mat 102 may cause portion 504 of sensing components 202 to provide greater input values, portion 502 of sensing components 202 may provide an increased output value (less than portion 504, greater than sensing components 202 not identified as portions 502 or 504). Accordingly, processor 204 and/or computer 414 may determine a plurality of contact points exist associated, at least in part, with usage of chair 404.

In other embodiments, chair 404 may comprise one contact geometry (e.g., pedestal), two contact points (e.g., "skid" type chairs), or three or more legs or wheels providing a non-zero number of contact points. Should zero contact points be detected, processor 204 and/or computer 414 may determine mat 102 is unoccupied. Seated humans, such as user 402, are known to provide a substantially uniform pressure with respect to those contact points accounting for the majority of the weight of user 402 and/or chair 404. Portion 502, which accounts for a trivial portion of the weight provided by user 402 in a seated configuration, may vary in terms of position and/or force measured. However, such motion may be discounted for points associated with a below-threshold amount. For example, if portions 502 account for ten pounds, while the aggregate of portion 504 accounts for two-hundred pounds (e.g., weight of user 402 and chair 404), processor 204 and/or computer 414 may then conclude portion 502 represent a user not standing (e.g. user 402). Additionally, portion 504 may move linearly in unison or rotate around a point upon mat 102. Based on at least the forgoing, user 402 may be determined to be seated.

Figure 6:
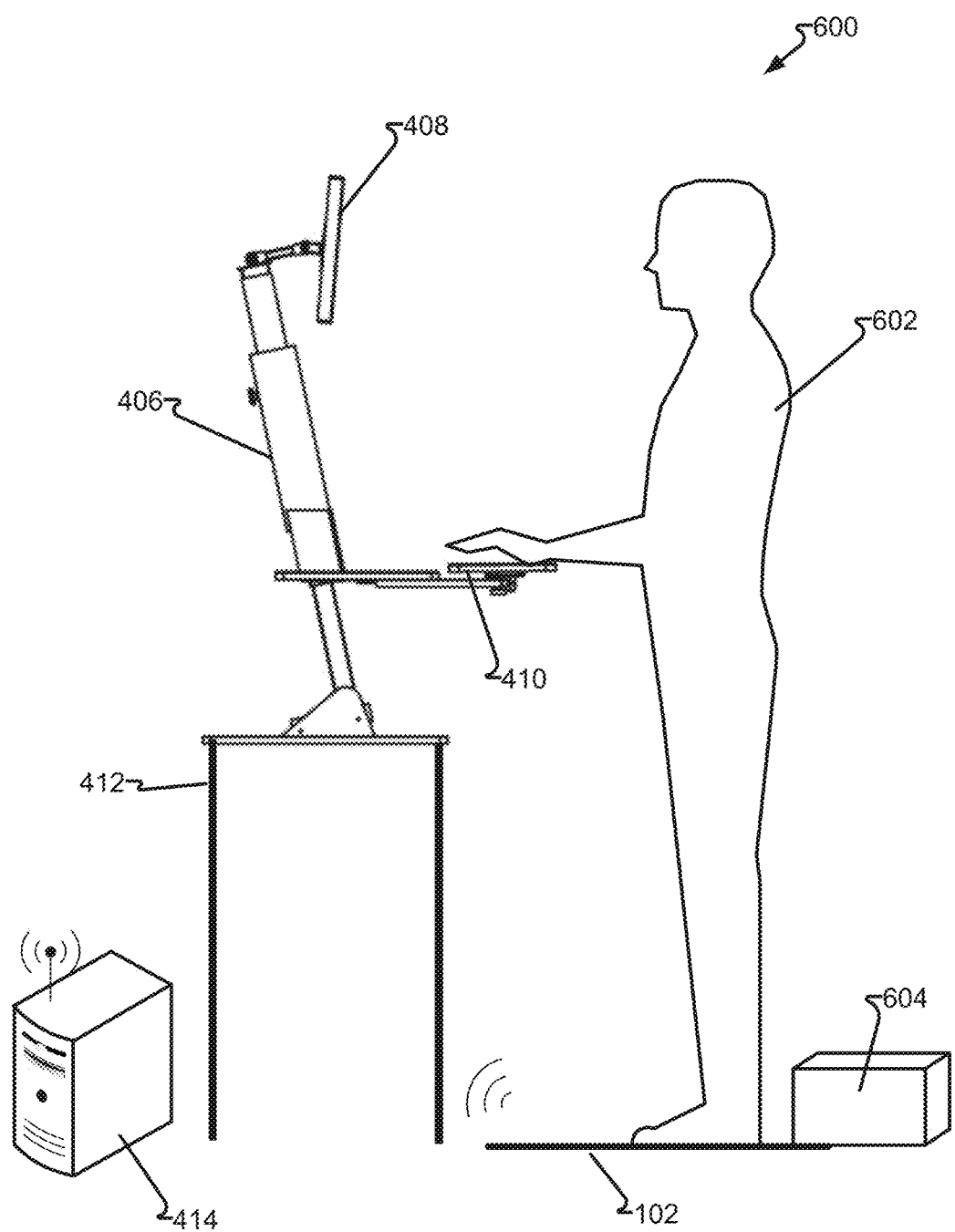
FIG. 6 depicts a second mat usage environment in accordance with embodiments of the present disclosure.

FIG. 6 depicts mat usage environment 600 in accordance with embodiments of the present disclosure. In one embodiment, user 602 is standing on mat 102 while using sit-stand desk 412 in a standing configuration. Mat 102, via processor 204 and/or computer 414, receiving inputs from sensing components 202. Mat 102 will then determine user 602 is standing. In another embodiment, mat 102, while in use by standing user 602 may comprise static non-zero readings from a subset of sensing components 202, such as due to box 604.

Figure 7:
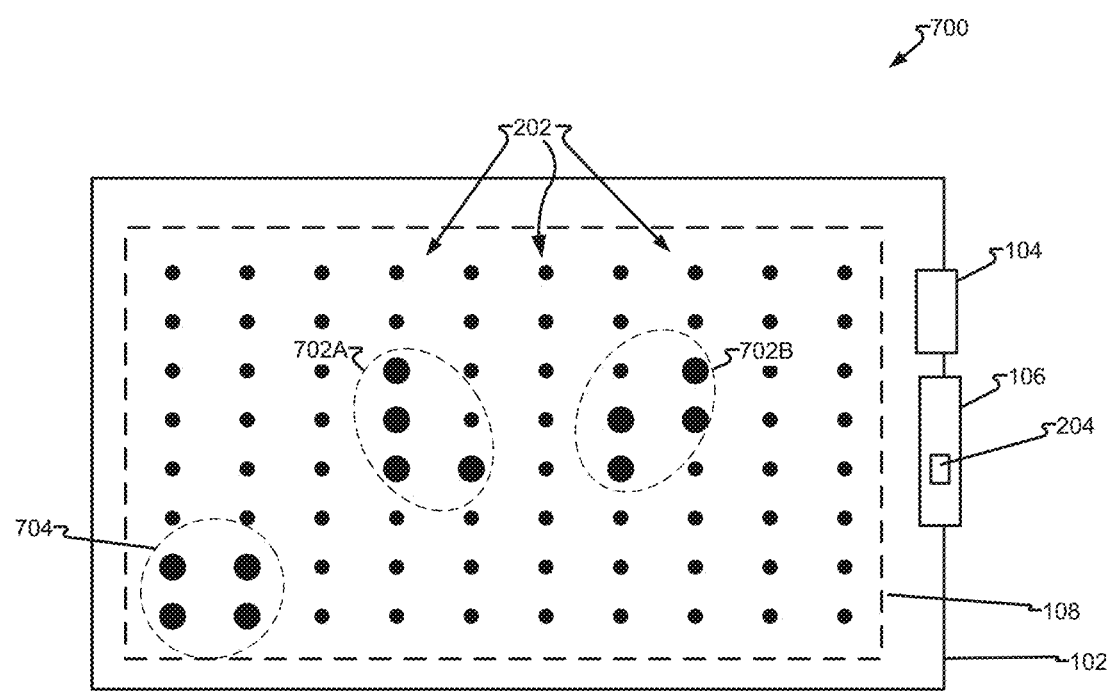
FIG. 7 depicts the mat as used in the second mat usage environment in accordance with embodiments of the present disclosure.

FIG. 7 depicts mat 102 with sensing components in accordance with embodiments of the present disclosure. In one embodiment, sensing components 202 are depicted as different sizes to indicate dissimilar pressure signal outputs, such as those detected when utilized in mat usage environment 600. Portion 702 may result from user 602, in a standing configuration, and providing pressure to at least a portion of portions 702A-B. Additionally or alternatively, portion 704 may result from box 604. It should be appreciated that a portion of a chair (e.g., chair 404) or other object may provide inputs resulting in portion 704.

It should also be appreciated that the number and/or distribution of sensing components 202 may be varied as a matter of design choice. As depicted in mat usage environment 700, user 602 is detected by some, but less than all, sensing components within portions 702A and 702B. Had additional sensing components been deployed within portions 702A and/or 702B, the geometry may be more foot or shoe-like, however, while denser placement of sensing components 202 may provide for a more precise image or may have other advantages, providing such a high resolution is not a requirement. In one embodiment, imaging provided by sensing components 202 reporting dissimilar pressures may be provided with as few as one of sensing components 202 reporting an additional pressure and one of sensing components 202 reporting an absence of additional pressure.

Figure 8:
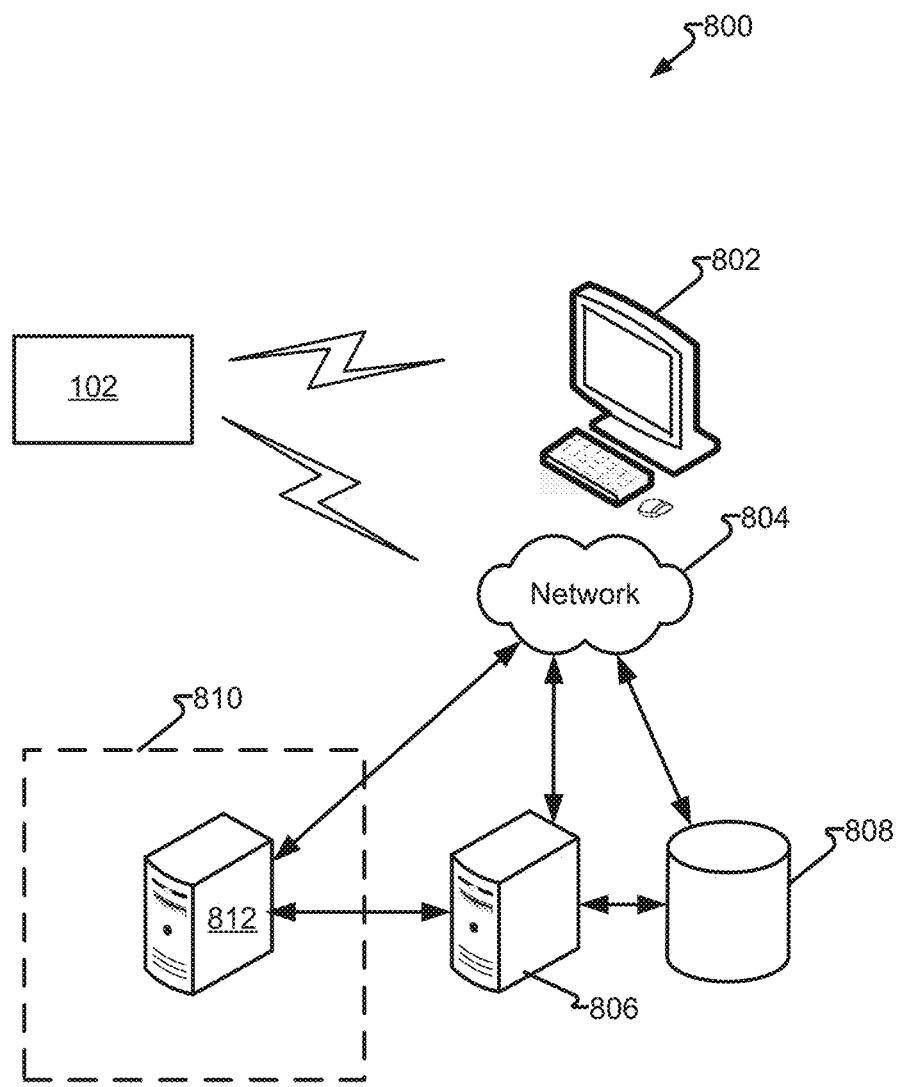
FIG. 8 depicts a first system in accordance with embodiments of the present disclosure.

FIG. 8 depicts system 800 in accordance with embodiments of the present disclosure. In one embodiment, mat 102 provides data signals of individual values for one or more sensing components 202 and/or processed values, such as from processor 204, for one or more sensing components 202. Data signals may be provided to local workstation 802, such as utilized by user 402 and/or 602 or a wellness manager or other personnel, which may be a dedicated device only monitoring one or more mats 102 or providing additional functionality (e.g., work processing, spreadsheets, communications, etc.), such as when workstation 802 is embodied as computer 414 in whole or in part. Additionally or alternatively, mat 102 may provide data signals, via network 804, to one or more of server 806 or database 808. As a further option, data signals may be provided and/or received from optional devices 810, which may include server 812 or other components (e.g., controllers, actuators, switches, relays, routers, etc.). In a further embodiment, data signals may utilize workstation 802 to connect to, and communicate via, network 804. It should be appreciated that additional or fewer components, or different configurations thereof, may be utilized to receive data signals, directly or indirectly and/or raw signals (e.g., readings from ones of sensing components 202) or processed data signals, without departing from the scope of the embodiments. Network 804 may comprise wired/wireless networks and may further comprise, in whole or in part, one or more networks such as the Internet, telephony, cellular, ethernet, Wi-Fi, Bluetooth, etc.

In one embodiment, data signals are received by a component, such as workstation 802 or other component comprising a data reception interface and/or network interface and at least one processor. Workstation 802, server 806, and/or processor 204 may receive data signals and provide additional processing. In one embodiment, workstation 802 determines if mat 102 is occupied or unoccupied. The determination of whether mat 102 is occupied or not is variously embodied and may comprise determining if the aggregate data signals provided by mat 102 indicate a weight that could be a human user. For example, mat 102 may indicate an aggregate detected weight is three pounds and, accordingly, may be due to an object, inaccurate readings from one or more sensing components 202, or other non-occupied cause. One target environment of mat 102 is for use by adults in the workforce, however, other environments, such as grade schools are also contemplated. As a result, the users of mat 102 may vary greatly in weight. However, certain minimum values, which may be further selected based upon a factory, administrator, or user configuration may be set and, any aggregate weight upon mat 102 that is below such a threshold value will be considered to be absent occupancy. While such a determination may be conclusive of a lack of occupancy, a detected weight above a minimum threshold may be insufficient to conclude occupancy. Accordingly, in additional or alternative embodiments, additional processing may be provided.

In another embodiment, sensing components 202 may detect static or dynamic variations in pressure and provide a corresponding output. The timeframe for which a determination of whether or not a data signal output by one or more sensing components 202 is considered static is variously embodied. The timeframe may be dynamically varied depending on the type of variations encountered. For example, a subtle swaying, whereby overall weight remains substantially constant, but increases with regard to sensing components 202 in one portion, such as portion 702A (e.g., detecting pressure from one foot) while decreasing with regard to sensing components 202 in another portion, such as portion 702B (e.g., detecting pressure from a different foot). Such subtle swaying may result in a dynamic signal over a short timeframe, such as less than 5 seconds. Additionally, the number of variations may be considered. In another embodiment, occupancy on mat 102 may be discarded entirely if observed for less than another threshold period of time. User 602 may stand on mat 102 for less than five minutes, as an example, and be considered an inconsequential occupancy and discarded as if there were no occupancy at all. Accordingly, outlier pressure readings from any one or combination of sensing components 202 that may indicate occupancy, but only last for less than a minimum threshold of time, such as a few seconds up to a few minutes, may be the result of another object (e.g., an object being dropped on or traversing mat 102) or an inconsequential usage of such a short duration that any health benefits gained are so minor than they may be discarded.

In another embodiment, the number and size of portions of sensing components 202 reporting pressure indicating occupancy may be evaluated. Humans will generally stand on two feet and produce two distinct portions of sensing components 202 indicating occupancy (e.g., portions 702A and 702B). The density of sensing components 202 and/or attribute of a standing user (e.g., standing with feet close together, amputee, etc.) may produce a single contact area. However, sway, aggregate detected weight above a threshold, shuffling, etc. will cause variations in the particular ones of sensing components 202 reporting pressure and/or the amount of pressure detected. Additionally or alternatively, standing user 602 may utilize a can, walker, or other standing device. Much like portion 704 of sensing components 202 reporting occupancy, if static, such as when the cane or walker is freestanding while the user is engaging with standing desk 412 or box 604 produces static portion 704, such static portions may be omitted from consideration. However, if such portions are not static (e.g., user 602 is utilizing a cane or walker while utilizing desk 412) then user 602 may be determined to be standing whether or not two or more portions of contact are detected.

However, not all dynamic pressure outputs are associated with standing use of mat 102. In another embodiment, a portion of sensing components 202 may indicate a path which may terminate, originate, or be maintained on mat 102. Such a path does not indicate standing use of mat 102 and may be caused a wheel of a chair or other object passing over mat 102. Accordingly, in another embodiment, dynamic changes in the number or indicated amount of sensing components 202 reporting pressure, when the pressure indicates a traversal path, may be considered a non-standing use of mat 102 and/or traversal by a wheel of a chair or other object. Accordingly, even if the detected object remains on mat 102, which may further be dynamic, such as when seated user 402 fidgets or provides other oscillations to mat 102 while seated. Therefore, portion 504 of sensing components 202 may be identified, via their traversal, as associated with non-standing use and even subsequent dynamic pressures may be considered a non-standing use.

Additionally or alternatively, seated user 402 may place their feet on mat 102 without a chair or other object being on mat 102. Portion 502 may detect occupancy and/or feet/shoes, such as when the density of sensing components is sufficient to indicate a feet/shoe geometry thereon. However, portion 502 are merely the feet of seated user 402. Sensing components 202 may indicate an aggregate weight across all sensing components 202 or only sensing components 202 associated with feet (e.g., portions 502A-B) to determine if a minimum weight is provided to indicate standing at a position associated with portions 502A-B. Additionally or alternatively, certain sensed activity of portions 502A-B may indicate a lack of standing. For example, standing user 602, even if swaying, jumping, etc. will provide an aggregate pressure indicating their weight when measured over a relatively short period of time as even a user jumping or otherwise moving on mat 102. Similarly, a swaying standing user 602 may reduce pressure on one foot while the add it to the other. A front-back sway can similarly be determined to be standing as pressure within a portion (e.g., portion 702A) will remain constant on the aggregate as individual sensing components 202 detect the variations within.

In contrast, seated user 402 may lift or otherwise shift their weight from of one foot without adding the corresponding decrease to the other foot. A feat that can be performed over a very short time (e.g., jumping, falling, etc.) by standing user 602 or routinely and/or indefinitely by seated user 402. If outlying observations are ignored, such as those occurring a single time and/or for a short duration (e.g., one minute, a few seconds or less) then user 602, even if falling or jumping may be determined to be standing while the reoccurrence of such observations for seated user 402 may indicate seated use of mat 102 and/or an absence of standing use of mat 102.

With usage of mat 102 determined (i.e., standing use or seated use) by workstation 802, server 806, and/or processor 204, additional operations may then be performed. In one embodiment, identification of a particular user may be provided. Profile information may be maintained, such as in database 808 or a memory associated with processor 204, computer 414, and/or workstation 802. Profile information may include information such as time/day of use and/or attributes of a particular user (e.g., weight, sway pattern, etc.). Accordingly, sensing components 202 may determine a particular pattern and/or amount of aggregate and/or individual pressure, oscillations, etc. and determine the identity of a user. However, conventional identification (e.g., sign-in, badge swipe, etc.) may be utilized as an alternate or additional means of authentication, such as to provide a more secure and/or more certain identification of a specific user.

In another embodiment, data recording may indicate utilization of standing to indicate use of a desk 412 in a standing configuration over one or more periods of time. For example, use of a particular asset (e.g., sit-stand desk 412) may be utilized in a standing configuration 39% of the time in the last month, 31% of the time the previous month, etc. User 602 stood for 29 hours last week, 35 hours the week before, etc. While data gathering and reporting are useful, other operations may be provided once it is known whether mat 102 is occupied and/or occupied in either for standing use or seated use.

In another embodiment, any occupancy of mat 102 may be utilized as a trigger to other systems or components. In other embodiments, occupancy in one of seated or standing or a transition (e.g., seated to standing, standing to seated, vacant to occupied, vacant to seated and/or standing, occupied to vacant, etc.) may be utilized as the trigger. For example, detecting a transition from unoccupied to occupied may signal optional devices 810, when embodied as heat, cooling, fan, lighting, etc., to operate in accordance with an occupied area. Similarly, a transition to unoccupied may cause optional devices to transition to an unoccupied mode of operation (e.g., turn off some or all lights, reduce heating/cooling, etc.). Computer 414 and may be configured to, at least partially, operate differently whether utilized by a standing or seated user as well as perform operations for a transition. For example, computer 414 may detect a transition from occupied to unoccupied and lock, enter a low-power mode, or other operation associated with an absence of a user.

Conversely, transitioning from an unoccupied to an occupied state may "wake" computer 414, such as to terminate a low-power mode of operation or perform other operation more conducive to being utilized rather than being unused by a user. Furthermore, knowledge of a specific user, either by identifying attribute (e.g., sign-in, weight, etc.) or by estimation (e.g., last user) may cause computer 414 to perform certain operations with such knowledge or assumed knowledge. For example, the user who comes in at 8:00 AM Monday-Friday typically uses sit-stand desk 412 in a standing configuration, therefore, when occupancy upon mat 102 is detected at 7:53 AM on a Tuesday, computer 414 which may further comprise a controller for support 406 and/or powered height-variable legs of desk, such as an actuator (not shown) of desk 412, to cause the worksurface to raise or otherwise accommodate standing use without requiring any further input or action to adjust the desk. Similarly, if a user is determined to utilize desk 412 in a seated configuration at 1:00 Monday-Friday, then support 406 and/or powered legs of desk 412 may lower to accommodate seated use when occupancy is detected at 1:09 AM on a Wednesday or alternatively lowered following detecting a transition to an unoccupied state of mat 102 at 12:03 PM (e.g., the user went to lunch and historically works in a seated position following lunch). As can be appreciated, a detected event, such as a transition from occupied to unoccupied or vice versa, may not trigger any action unless it occurs at a specific time or within a particular time window. Additionally, the time or time window may be provided or learned, such as the occurrence of a manual transition (e.g., raising or lowering) that occurs over many observations to develop a probability curve. A particular probably threshold may then be utilized, such as a user who starts work at 8:00 AM, and has a two-standard deviation time window that covers 7:43 to 8:21 and may be considered to be the trigger. However, anything outside of that time window may have a probability that may or may not indicate a particular usage and, accordingly, disabled. For example, a user's workstation may be available to any user if the assigned user does not show up by 8:30 AM.

In another embodiment, a request (manual or automated) to transition desk 412 from standing use to sitting use, or vice versa, may signal computer 414, such as when mounted to support 406 and/or comprising monitor 408, to alter its operations accordingly. For example, users generally are farther away from monitor 408, when standing, as compared to when seated. Accordingly, transitioning from seated to standing configuration may cause computer 414 to enlarge the text or other display components presented on monitor 408 or, when transitioning to seated, reduce the size of text or other visual components. A computer mouse, keyboard, or other motion sensitive component may then operate at a reduced sensitivity to accommodate a user standing as compared to seated.

In another embodiment, workstation 802 may comprise a processor executing instructions that time a user's mode of operation and provide alerts and/or automatic actions. For example, user 402 may have been seated for three hours and, in response, workstation 802, when embodied as computer 414, may present a pop-up message on monitor 408, send a text message, or send other communication to user 402 to prompt user 402 to transition to standing. Similarly, a user may "overdue it" if they stand to long and similar alerts may be provided to users who stand beyond a threshold duration. Additionally or alternatively, desk 412 may automatically transition from one mode of use to the other based on time of day, day of week, duration of usage in one mode, aggregate duration over two or more days in one mode, etc.

Mat 102 may be utilized at a dedicated workstation for a particular user. Accordingly, in certain embodiments, mat 102 may assume use thereof is use by the particular user. In other embodiments, mat 102 may be utilized in a shared workspace, such as a conference room or in close proximity to one or more other mats 102. As a result, associating a user with a specific one of mat 102 may be necessary. When communication interface 106 is a wired connection to workstation 802 a user may be identified via sign-in on an application executed on workstation 802. When communication interface 106 is a wireless connection to workstation 802 or workstation 802 is not paired with mat 102, a user may be prompted to identify themselves. For example, one of a plurality of mats 102 may issue a prompt a user to step off then back on. The prompt may be on a specific one of workstations 802 utilized by a known user. If the user complies, then workstation 802 may identify the particular one of mats 102 being utilized by a particular user. Tapping, swiping, or other motions, which may be required to be performed within a particular time window, may be utilized to identify a particular user. An application, such as one executing on server 806, workstation 802, or processor 204 of a designated mat 102 may coordinate authentication/identification so that no two mats 102 request the same authentication/identification activity or, if the same activity is requested, different timeframes are utilized.

Figure 9:
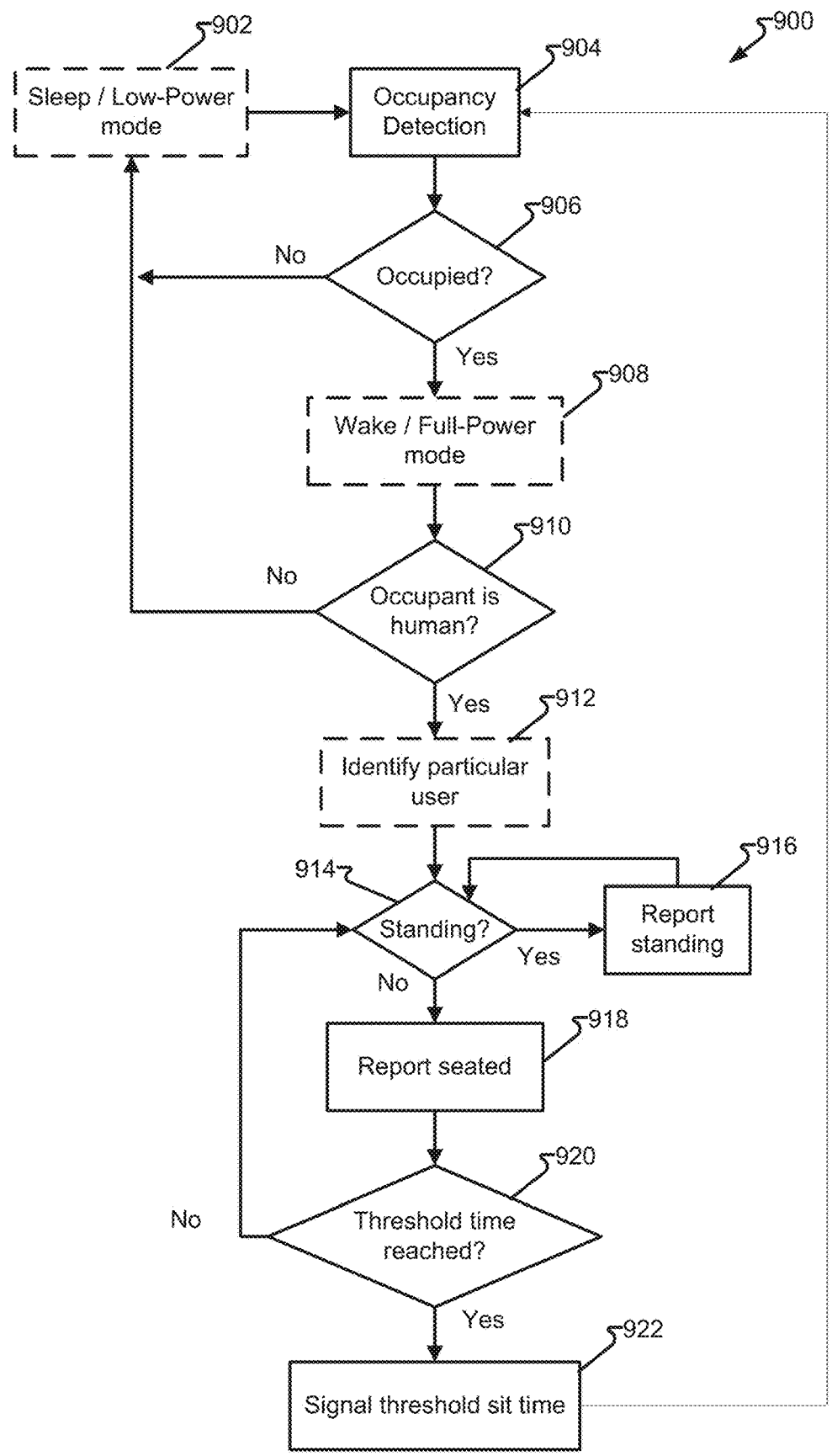
FIG. 9 depicts a first process in accordance with embodiments of the present disclosure.

FIG. 9 depicts process 900 in accordance with embodiments of the present disclosure. In one embodiment, step 904 detects occupancy. Step 904 may detect a lack of any sensed pressure, or a detected pressure below a previously determined threshold, on mat 102 as an absence of occupancy. Test 906, in conjunction with the operations of step 904, then response according to whether occupancy is or is not detected. If test 906 is determined in the negative, process 900 may continue back to step 904 to continue monitoring for occupancy. Optionally, step 902 may initiate or maintain a lower-power mode (e.g., sleep, power-off, etc.) in response to test 906 being determined in the negative. If test 906 is determined in the affirmative, processing may continue to test 910. Optionally, step 908 may initiate or maintain a wake state (e.g., full power). Step 902 and/or test 910 may manage the power utilization of mat 102 or another component, such as computer 414, workstation 802, optional devices 810, etc.

Next, test 910 may identify whether occupancy is caused by a human or non-human (e.g., leg or wheel of a chair, box, etc.). Test 910 may determine that there is a periodic motion, such as a sway, that is associated with human use. Other motions, such as sliding, tapping, etc. may also be associated with a human. Static pressure readings (e.g., no variation over a previously determined period of time) for all or a portion of non-zero pressure readings for a particular portion of mat 102 (e.g., portion 704), may indicate a "stuck" sensor or a non-human object (e.g., box, leg of a chair, etc.). Accordingly, test 910 may consider such points as non-human and eliminated from further consideration. If no points then remain, test 910 may be determined in the negative. However, if at least one point or portion of non-zero pressure indicates a sway, shift, or other motion associated with a human, test 910 may be determined in the affirmative.

Optionally, step 912 may identify a particular user. A database, such as database 808 or other data storage, may comprise records associating a particular pressure pattern observed by mat 102 with a known user. A known user may be expressly identified (e.g., "John Smith") via login or other data entry means or categorized (e.g., the same user as yesterday, a user different from the previous user, a user different from "John Smith," etc.). Accordingly, if a recognized pressure pattern is encountered, the user may be identified and an action perform in accordance with the user (e.g., place the height of desk 412 at the configured height desired by the identified user, cause a computer to load an associated profile, etc.).

Test 914 determines if the usage of mat 102 is a standing usage or a non-standing usage. Test 914 may determine if portions of pressure on mat 102 that have non-static values (e.g., portions 702) have at least a minimum threshold aggregate weight, position, variations, etc. that indicate a user is standing on mat 102 and, thereby, cause test 914 to be determined in the affirmative. Optionally, test 914 may determine whether the usage is a seated usage. For example, if dynamic portions (e.g., portions 502) fail to provide an aggregated weight associated with a user or a usage pattern that indicates seated use (e.g., one portion, such as portions 502A, may be decreased without a corresponding increase in another portion, such as portions 502B, or an corresponding increase in more than two points, such as portions 504). If test 914 is determined in the affirmative, process 900 may then continue to step 916 whereby the user may be reported as standing. Step 916 may comprise updating a record, terminating a "time seated" timer, signaling a component to alter operations (e.g., raise desk 412 for standing use, etc.).

Figure 10:
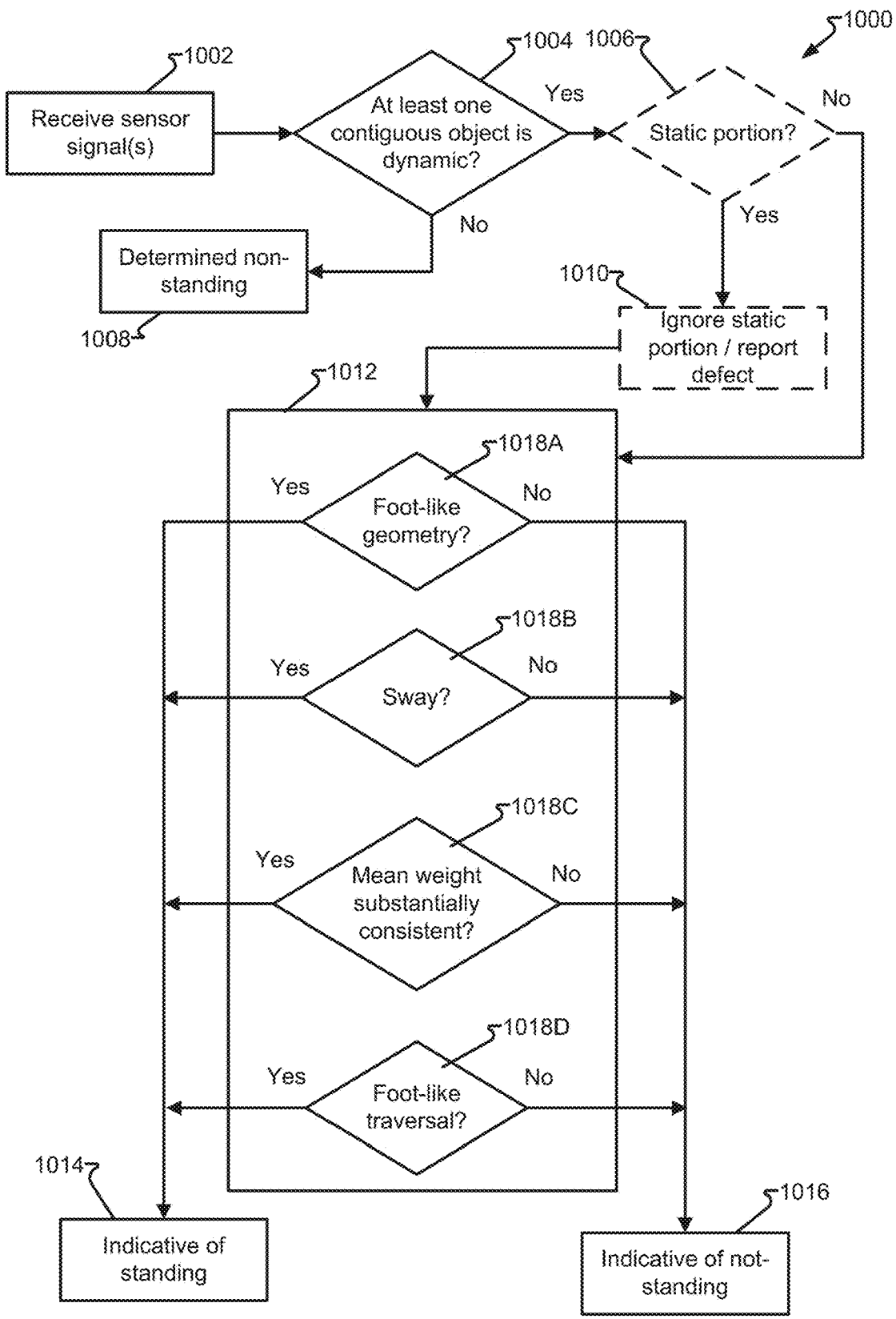
FIG. 10 depicts a second process in accordance with embodiments of the present disclosure.

If test 914 is determined in the negative, process 900 may then continue to step 918 whereby the user is reported as seated. Step 918 may comprise updating a record of time spent seated, start or continue a "time seated" timer, signal a component to alter operation (e.g., lower desk 412 for seated use, etc.). In another embodiment, test 920 determines if the "time seated" exceeds a previously determined threshold. If no, process 900 may continue back to test 914. If test 920 is determinized in the affirmative, step 922 may imitate a signal. The signal may be a message sent to a user (e.g., pop-up message on computer 414, text message, vibration on mat 102, update record, etc.). It should be appreciated that other embodiments, such as resuming process 900 at step 904 and/or test 910, another point may be provided, such as when test 920 is determined in the negative or following step 922, without departing from the scope of the embodiments. As a further option, time or duration spent seated or standing may be reported and utilized for various triggers, such as a congratulatory notification upon standing for a previously determined duration or having stood for at least a particular number of times in given day, week, etc. Process 900 may operate intermittently, periodically, and/or continually FIG. 10 depicts process 1000 which may comprise, in whole or in part, step of test 914 to determine if a user is standing in accordance with embodiments of the present disclosure. As a further option, process 1000 may comprise additional or alternative steps otherwise provided in process 900. In one embodiment, step 1002 receives signals indicating pressure and/or location of pressure from mat 102. Next, test 1004 determines that mat 102 comprises at least one portion providing dynamic values. It should be appreciated that the timeframe to determine whether or not a value is dynamic may be selected in accordance with human physiology and what may be utilized to determine a human stance. For example, small motions of a human standing stationary may be detected over a period of a few seconds or less, such as five or ten seconds. A human in a more normal mode, may impart variations observed on mat 102 within one second or less. A pressure sensing area that is entirely static for a longer period of time one minute or more may be determined to be non-human (e.g., box, chair leg, etc.). As a human may occupy mat 102 along with a non-human object (e.g., user standing while a box also rests on mat 102), only dynamically varying portions may be considered further for human occupancy and/or sitting/standing determinations. If test 1004 determines there is not at least one dynamic portion, test 1004 may be determined in the negative and step 1008 determines use is a non-standing use. Step 1008 may further consider the use to be non-use (e.g., lack of occupancy) or static use (e.g., presence of an inanimate object on mat 102). If test 1004 is determined in the affirmative, step 1012 may then be executed. Optionally, test 1006 and step 1010 may be performed. Test 1006 determines if there is a static portion in addition to the at least one dynamic portion. If no, processing may continue to step 1012. If test 1006 is determined in the affirmative, step 1010 may report the object to a user, maintenance personnel, or other system or component, such as to indicate a defect (e.g., "stuck" pressure sensing component) or misuse (e.g., chair or table leg on mat 102). Following step 1010, processing may resume at step 1012.

Step 1012 comprises one or more criteria 1018 utilized to determine if a user is standing or not standing or, additionally or alternatively, seated. Certain criteria 1018 may provide a conclusive determination, such as to override or omit other criteria 1018. For example, criterion 1018C registers only a few pounds that varies to zero—associated with a seated user lifting their foot. Other criteria 1018 may provide support or a lack of support for a particular determination provided by other criteria 1018. For example, criterion 1018A may indicate a foot or shoe-like geometry is pressing on mat 102. However, as feet and shoes vary considerably in their size and geometry (e.g., high-heals versus running shoes versus dress shoes, etc.), such a determination may not be conclusive. However, if criterion 1018B indicates a sway associated with a human standing, the determination may be more certain. Conversely, if criteria 1018 indicates no sway or a weight not associated with a human occupant on mat 102 (e.g., a user left their shoes on the mat), then the confidence that a user is standing may be less certain or discounted entirely. Step 1012 then utilizes the one or more criteria 1018 to determine whether the user is standing, and thereby executing step 1014, or not-standing, and thereby executing step 1016. Steps 1014 and 1016 may cause a component to perform a particular operation, such as raise/lower desk 412, cause workstation 802 to operate in a mode for seated use (e.g., smaller font, accept fine inputs on a mouse or other tactile input component) or standing use (e.g., larger font, ignore fine inputs and only consider coarser inputs on a mouse or other tactile input component).

Criteria 1018 is variously embodied and may include criteria 1018A-D, such as to evaluate wither a foot or shoe-like geometry is detected, sway is detected, a mean weight of dynamic portions is substantially constant, a foot or shoe-like traversal, etc.). It should be appreciated that other criteria may also be implemented. For example, criterion 1018D determines if a sensed portion on mat 102 is foot-like. For example, a linear or curvilinear path may be indicative of a wheel of a chair and, therefore, not a standing user at least with regard to the sensed portion. However, if a sensed portion of mat 102 indicates a user stepping onto mat 102, then the user is, or is likely, standing. In another embodiment, timing or duration is considered. For example, an indication of seated use, when previously determined to be a standing use, or vice versa that lasts for less than three seconds, may be ignored as an anomaly. The specific duration may be selected in accordance with learned behaviors or previously determined threshold values to balance responsiveness with the duration of anomalies.

Figure 11:
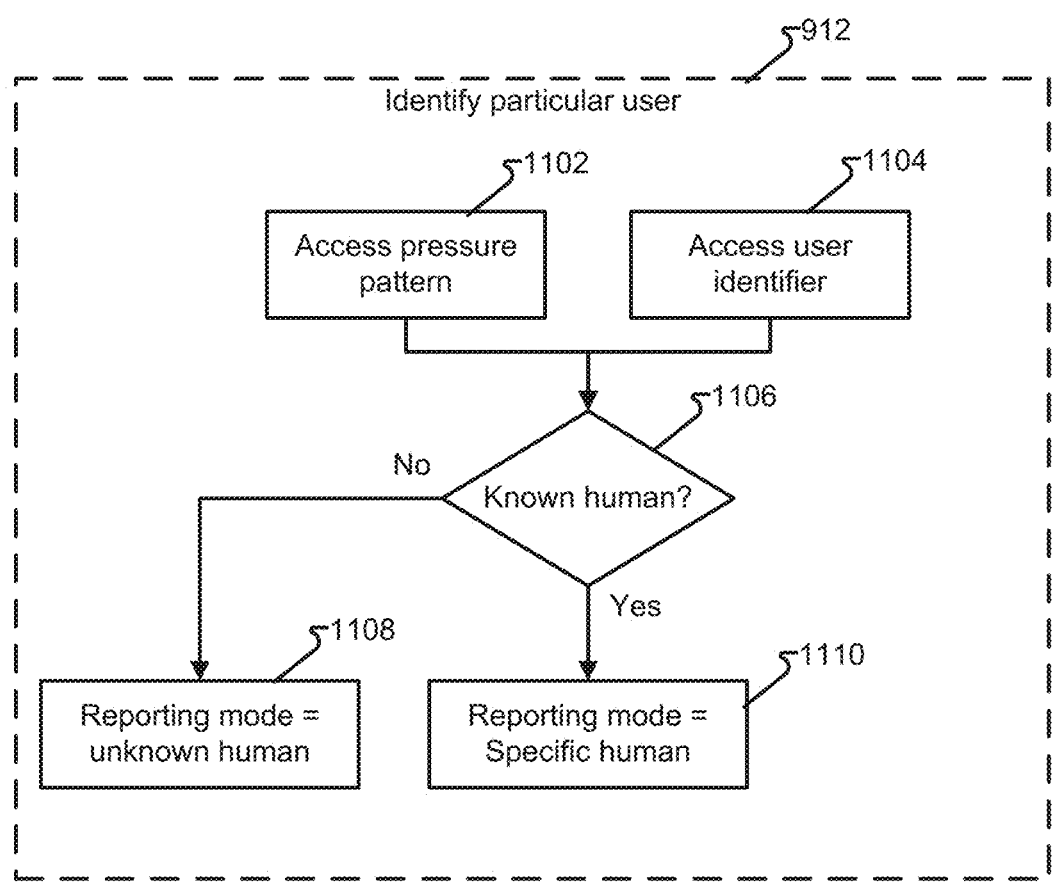
FIG. 11 depicts a third process in accordance with embodiments of the present disclosure.

FIG. 11 depicts process of step 912 in accordance with embodiments of the present disclosure. Step 912 may be executed to determine the identity of a particular human occupant on mat 102. In one embodiment, each of steps 1102 and 1104 are executed. Step 1102 accesses a record associated with a particular pressure pattern observed on mat 102. Step 1104 accesses an identifier of users and associated recorded pressure patterns. Test 1106 determines if the observed pressure pattern matches one of the recorded pressure patterns. If test 1106 is determined in the negative, step 1108 is executed whereby operation of mat 102 and/or associated components is performed in a mode associated with an unknown user, such as to prompt the user to sign-in, or otherwise identify themselves, or to operate in an anonymous user-mode. If test 1106 is determined in the affirmative, step 1110 the operation of mat 102 and/or associated components is performed in a mode associated with the identified user, such as to cause a component to be configured in accordance with a setting for the known user.

Figure 12:
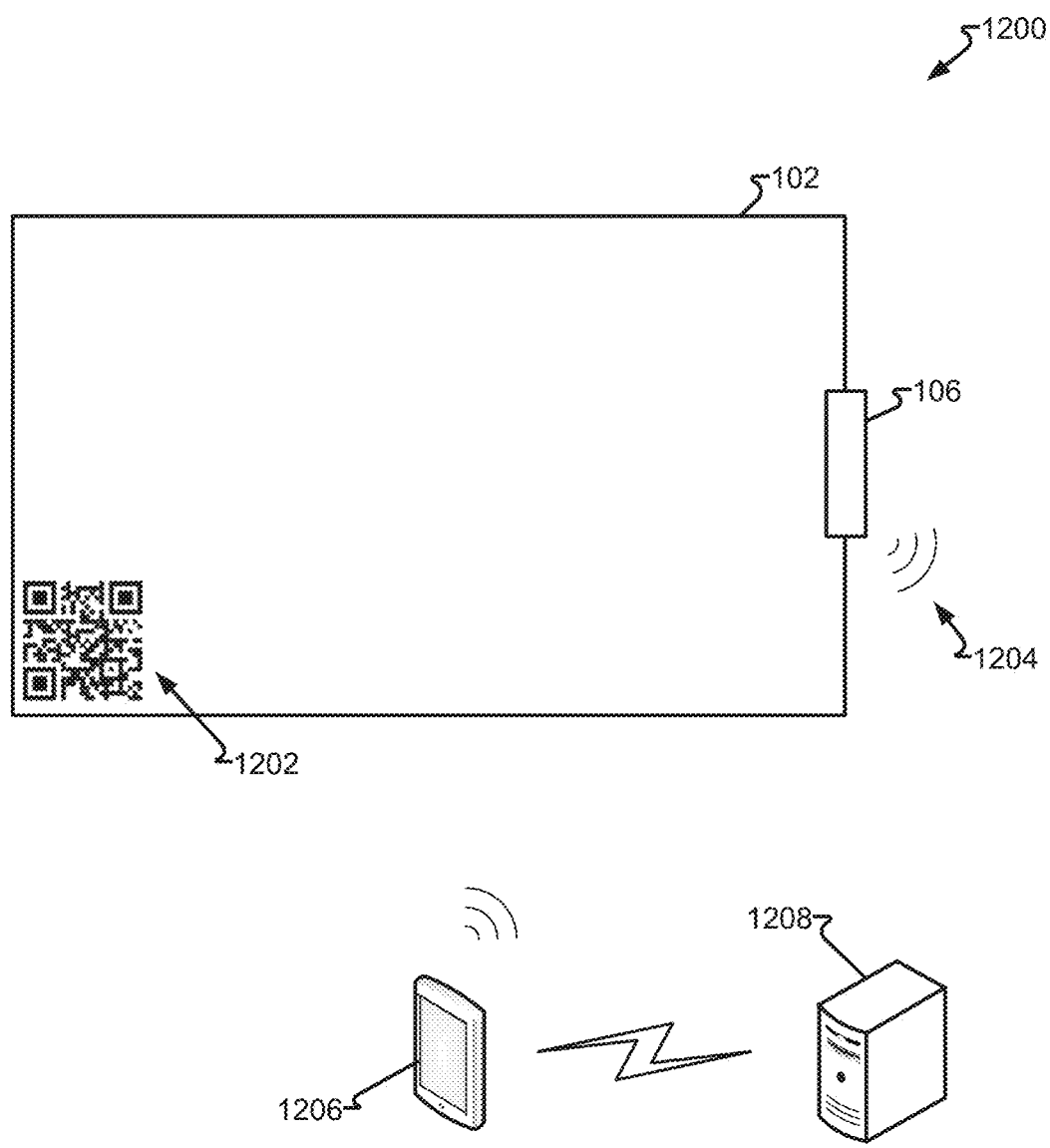
FIG. 12 depicts a second system accordance with embodiments of the present disclosure.

FIG. 12 depicts system 1200 in accordance with embodiments of the present disclosure. In one embodiment, mat 102 identifies a user of mat 102. In one embodiment, use of mat 102 comprises standing on mat 102 by the user. In another embodiment, use of mat 102 comprises siting on a chair that, in whole or in part, rests on mat 102. In yet another embodiment, use of mat 102 comprises being proximate to mat 102, such as to be identified (as described herein) by mat 102 and/or the user, such as by communication device 1206, identifying mat 102. Use of mat 102 may be intermittent. For example, a user may be on, and then off, a number of times within a relatively short period of time (e.g., within a work shift) such as may be characteristic of a user working at workspace having mat 102, and standing/siting thereon, and leaving mat 102 to tend to other tasks.

Use of mat 102 may be, or is expected to be, limited to a single individual, one of a finite set of individuals (e.g., workers who are authorized to access a workspace having mat 102), semi-private (e.g., any user who is in a school, a guest of a hotel, within an airport lounge, etc.), or public (e.g., anyone who decides to enter a public library or other public space, such as a shopping center, public area of an airport, etc.). In other embodiments, it may be important to identify who is not the user of mat 102. For example, if a workspace having may 102 is utilized by an infected user, another user who is known to be elsewhere when the contagion may be transmitted, may be eliminated and resources directed to contact tracing those what could have been exposed or who cannot be eliminated from a pool of potentially exposed individuals.

Exposure, or potential exposure, to contagion may be limited to known transmission pathways for a particular contagion. If a pathogen is viable on a surface (e.g., doorknob, break room surfaces, etc.) for a period of time, then any individual who interacts with such a surface, within the period of time the surface was visited by an infected person, may be considered to be exposed and potentially infected. However, if the contagion is considered to be only spread when people are closer than a particular distance, then only individuals who got closer to an infected (or suspected infected) individual may be considered to be exposed. Conversely, individuals who never got closer than the particular distance (or second distance greater than the particular distance) may be considered to be not exposed.

In order to facilitate contact tracing of infected (or suspected infected) individuals and other parties, mat 102 and systems comprising mat 102 may be utilized to identify persons involved in a potential transmission and/or eliminate individuals who are determined to not be involved in a potential transmission. Accordingly, and in one embodiment, a user of mat 102 may be determined. Mat 102 comprises communication interface 106. In one embodiment, communication interface 106 further comprises radio frequency signal 1204, such as Bluetooth, near-field communications (NFC), cellular, WiFi, and/or other radio signal comprising an encoded identification of mat 102 and/or identification of a communication device, such as communication device 1206, when within communication range of each other. Additionally or alternatively, mat 102 may comprise visual identifier 1202. Visual identifier 1202 may be a QR code, bar code, Snaptag, Microsoft tag, etc. that, when captured by a camera (not shown) of communication device 1206 associated with a user, wherein communication device 1206 communicates with mat 102 and/or server 1208, to pair mat 102 with communication device 1206. The pairing may exist until a de-pairing event occurs, such as mat 102 becomes idle for a previously determined period of time, communication device 1206 becomes paired with a different mat 102 and/or a component at a different location from mat 102, communication device 1206 is no longer in communication with mat 102, and/or a different communication device (associated with a different user) is paired with mat 102. Server 1208 may be a dedicated server to one or a plurality of mats 102, general purpose server, networked server, public shared appliance (e.g., "cloud" server) connected to mat 102 and/or communication device 1206 via private network and network connectivity (e.g., Ethernet, WiFi, Bluetooth, etc.), public network (e.g., Internet), or a combination thereof.

In another embodiment, pairing of mat 102 with a user may be provided by accessing a computer or other sign-in device proximate to mat 102. Additionally or alternatively, communication device 1206 may scan a visual code and/or radio frequency paring with a different component physically proximate to mat 102. For example, a keycard may be utilized to unlock a computer (not shown) or access other resource. The computer and/or resource may then communicate via communication interface 106 of mat 102 and vice versa. A sign-on and/or pairing may perform other actions, such as setting a workstation, utilized with mat 102, to a user's preference (e.g., raising/lowering the height of a worksurface, monitor, keyboard, etc., setting lighting, heating/cooling, and/or other environmental controls, routing telephone communications to a telephony endpoint near the workstation, etc.).

While pairing of communication device 1206, which is personal and specific to a user, with mat 102 provides one means to specifically identify an individual user of mat 102 and/or to eliminate other potential users from consideration while utilized by the identified user. In another embodiment, a user may be identified from biometrics provided by the user's current and/or past interactions with mat 102. For example, a user of mat 102 may have an overall weight, standing pattern, shifting pattern (e.g., shifting from one foot to the other while standing, shifting weight from one part of a foot/feet while standing), tapping, and/or other motions. Such a user, even if not specifically known, may provide identifying attributes of the user or, to a subset of users. A data storage of mat 102 and/or server 1208 may maintain records of use for a number of users and their biometric patters. Accordingly, at the time of a potential transmission of a contagion, a user engaged with mat 102 may have a biometric pattern matching, or sufficiently matching, the user of mat 102 and/or a different mat, at a prior time. Accordingly, the user at the time of potential transmission can be identified as also being a user of mat 102 (or a different mat) at a prior time to further eliminate unknown candidates as the user and/or identify the user. Biometric patters may also be determined from a pattern of use. For example, a user who routinely needs to step away from their workstation would have a pattern of being on and off mat 102. Accordingly, an unidentified user that has the same pattern of being on and off map 102 may be, or be considered a candidate match. Similarly, a user's who, once on mat 102, is rarely or has limited periods of being off mat 102 and may be excluded as matching the current user.

Figure 13:
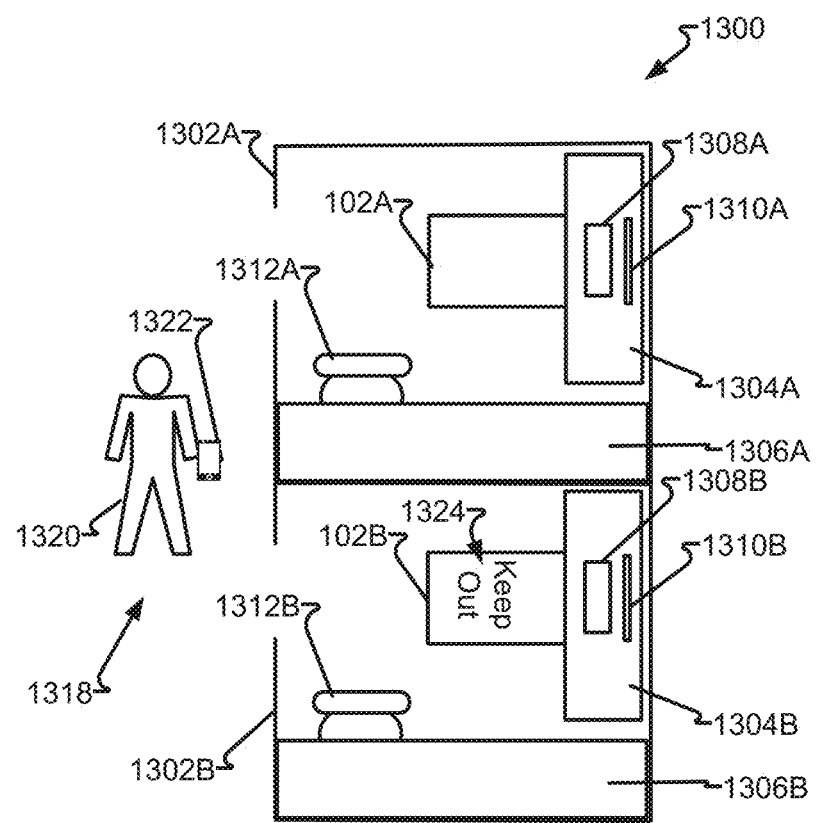
FIG. 13 depicts a work environment in accordance with embodiments of the present disclosure.

FIG. 13 depicts work environment 1300 in accordance with embodiments of the present disclosure. In one embodiment, work environment 1300 comprises work areas 1302. Work areas 1302 may further comprise similar or dissimilar collection of furniture and equipment, such as work surface 1304, work surface 1306, keyboard 1308, monitor 1310, and chair 1312. In one embodiment, work area 1302A has therein mat 102A and work area 1302B has therein mat 102B. In one embodiment, work areas 1302 are private offices where interaction between occupants while in each of work area 1302A and 1302B, is minimal (assuming proper ventilation ducting of work areas 1302).

In one embodiment, work areas 1302 are separated by no or partial walls (e.g., cubical partitions) where interaction between occupants while in each of work area 1302A and 1302B, is potentially sufficient to transmit a contagion. For example, a user of mat 102 while standing may be more likely to expose, or be exposed, to a contagion present in a current or recent user of work area 1302B. Accordingly, if a user of work area 1302A may be considered too far to transmit a contagion to a user of work area 1302B if seated substantially all of the time, but close enough to transmit the contagion if standing. The distance may be reduced further if each of the users, of work area 1302A and 1302B, are both using mat 102A and 102B, respectively, while standing. Seated use of mat 102A and/or 102B may be determined by a pressure pattern and or wheel tracking patterns of legs or wheels of chair 1312A and/or 1312B, respectively, on mat 102A and/or 102B, also respectively.

Mat 102A and/or mat 102B may be proximate to other people, such as user 1320 in hallway 1318. User 1320 may carry communication device 1322. As such mat 102A and/or mat 102B may detect the passage of user 1320 via radio frequency signals, including but not limited to, Bluetooth. Accordingly, if a user of work area 1302A, 1302B, or user 1320 is identified as infected with a contagion, mat 102A, mat 102B, and/or server (e.g., server 1208 in communication with mat 102A and 102B) may have a record of the encounter and those in proximity to the infected person for a period of time—such as a period of time the contagion is considered to be a viable outside of an infected person.

In another embodiment, the use of mat 102 by an infected person may require prompt action to hinder further spreading of the contagion. For example, mat 102A and 102B may be available on a first-come basis. Accordingly, display, such as display 1324, may be integrated into mat 102B, for example. If work area 1302B is available the message may be a welcome message (e.g., "Sign-in to get started," "Welcome Hotel Guest," "Work area available," etc.). However, if mat 102B is determined to be unsafe, such as due to a potential exposure to a contagion, display 1324 may provide a notification message, such as "Keep Out!", until such time as work area 1302B (and any additional areas) are sanitized or otherwise deemed safe for use (e.g., the suspected infected user was subsequently determined not to have the contagion). In another embodiment, notification to an access control system (e.g., electromechanical lock, badge/card reader, biometric reader, etc.) may be notified and automatically restrict access to an area suspected of having an active contagion. In yet another further embodiment, users currently at a location that is deemed at-risk for the contagion may be provided with an automatic notification to leave and/or have components disabled (e.g., a computer or other equipment utilized within work area 1302A and/or 1302B may be locked or powered off in response to a signal from mat 102A, 102B, and/or server 1208 in communication with mat 102A and/or 102B and the respective external device (e.g., security system, display, access control system, etc.).

Figure 14:
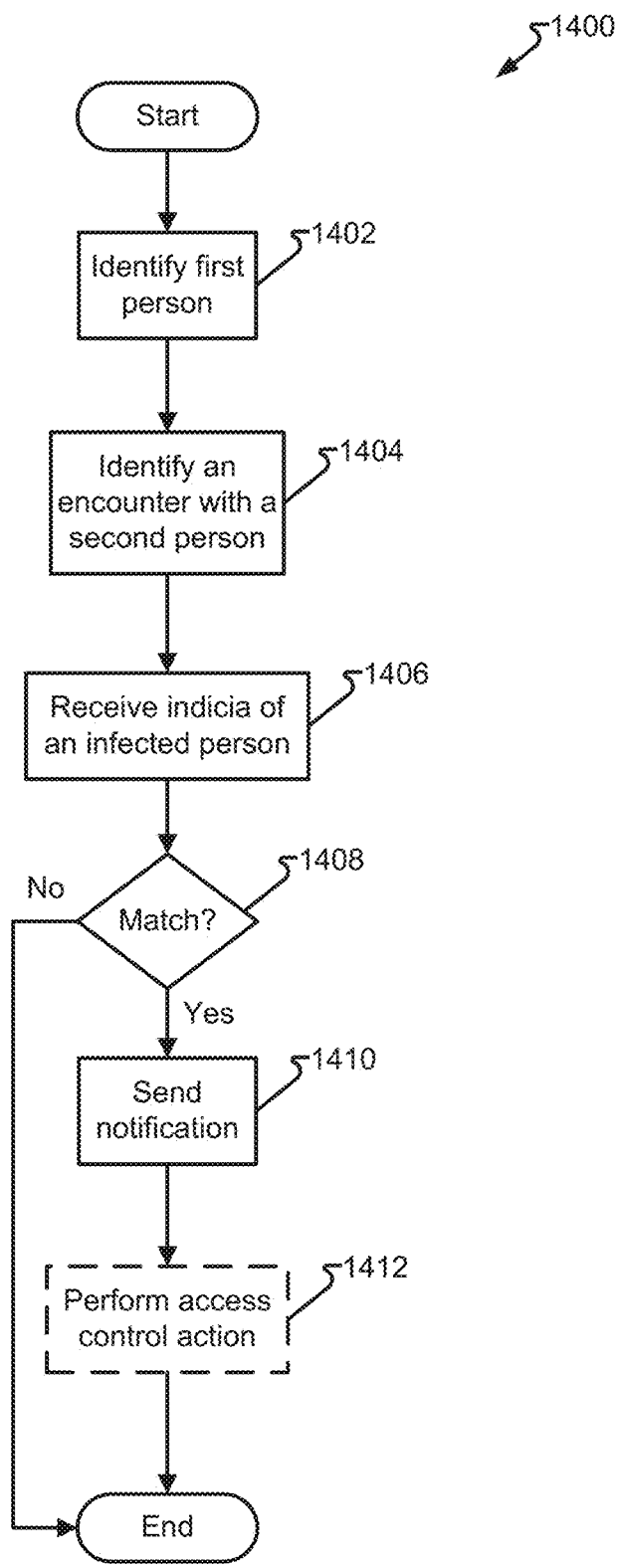
FIG. 14 depicts a fourth process in accordance with embodiments of the present disclosure.

FIG. 14 depicts process 1400 in accordance with embodiments of the present disclosure. Process 1400 may be executed as machine-readable instructions for execution of a processor, such as a processor of mat 102, server 1208, and/or other electronic processing device. It should be apparent to those of ordinary skill in the art that certain steps of process 1400 may be performed in the order illustrated or, in other embodiments, a different order.

In step 1402 a first person is identified, such as by methods and systems described elsewhere herein. Step 1402 may comprise the identification of a specific individual, such as by entering an identification number, swiping or scanning an access badge or card, entering a username and/or password into a computing system, etc. The component or system utilized to receive the identification may then interface with mat 102 and/or server 1208 to maintain a record in a data storage memorializing the usage.

In another embodiment, step 1402 may identify a characteristic of the first person, such as via a biometric indicator or pattern, such as an overall weight as observed by mat 102, a pattern of standing (e.g., shifting weight, tapping, etc.), foot/shoe size, frequency/pattern of getting on and off the mat, etc. Step 1402 may attempt to identify the person the first person by matching a data record maintained in a data storage device of, or accessible to, mat 102 and/or server 1208. If a match to another record is determined, the other record may provide a specific identification of the user (e.g., a prior usage of mat 102 where they explicitly identified themself) or, at least, the knowledge that the user was also utilizing mat 102 at the prior time. It should be appreciated that a prior usage of mat 102 may be the same or a different mat.

In another embodiment, step 1402 may identify a user that is proximate to mat 102 without actually utilizing mat 102, such as a passerby who was able to be identified via a Bluetooth or other radio frequency signal.

Similarly, step 1404 identifies an encounter with a second person, such as by methods and systems described elsewhere herein. The encounter may be a "live" encounter, such as when two people are having a face-to-face conversation; a proximity encounter, such as when two people are generally in the same area at the same time; and/or an indirect encounter, such as when two people occupy generally the same space but at a different time, however the time difference is sufficient to enable transfer of a contagion from the first person to the second person or vice versa.

Step 1406 receives indicia of an infected person. In one embodiment, the indicia identifies a specific individual (e.g., name, user name, member number, etc.). Accordingly, step 1406 may determine what, if any, mat 102 and/or other locations or equipment may be impacted. In another embodiment, a data storage comprising biometric patterns of usage for one or more mats 102 may be accessed. For example, if the infected person is a known user of mat(s) 102, then records in a database having the biometric records of the infected user may be identified, such as with records of non-specifically identified individuals. Accordingly, if a match is discovered, then then infected person may be determined to have utilized a particular mat(s) 102.

In another embodiment, a "best match" may be performed, such as to eliminate users of mat(s) 102 that are definitively not the infected person and/or to identify users of mat(s) 102 that are or are sufficiently likely to be the infected person.

Test 1408 determines if a match is found between ether the first person or the second person having had the encounter. If test 1408 is determined in the negative, process 1400 may end or be repeated for a different first person, second person, and/or indicia of an infected person. If test 1408 is determined in the affirmative, then step 1410 sends a notification to an external component. The external component is variously embodied and may comprise, but is not limited to, server 1208, display 1324 of one or more mats, communication and/or computing devices (e.g., text messages, emails, etc.), and so on. Accordingly, individuals who have had an encounter with the infected person or other resources (e.g., sanitization personnel, medical personnel, workforce allocation personnel, security personnel, etc.) may be notified. Optionally, automatic measures may be performed in step 1412 without requiring human intervention. Such actions include, but are not limited to, automatically displaying signage to display a warning to stay away, locking/unlocking access points, disabling systems to discourage their current and/or future use, minimizing interactions between suspected infected personnel with other personnel, such as denying access to a previously authorized area and/or granting access to a previously unauthorized area.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor (GPU or CPU), or logic circuits programmed with the instructions to perform the methods (FPGA). These machine-executable instructions may be stored on one or more machine-readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process, which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine-readable medium, such as a storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While illustrative embodiments of the disclosure have been described in detail herein, it is to be understood that the inventive concepts may be otherwise variously embodied and employed, and that the appended claims are intended to be construed to include such variations, except as limited by the prior art.

What is claimed is:

1. A system for responding to a potential contagion transmission, comprising:
    a pressure sensing mat comprising a plurality of sensing portions;
    a processor receiving signals from the plurality of sensing portions;
    a communication interface facilitating communications between the processor and a number of external components; and
    wherein the processor:
        identifies a first person having used the pressure sensing mat;
        identifies an encounter between a second person and the first person having a distance therebetween that is less than a transmission range of a contagion;
        receives indicia of an infected person;
        upon determining that the indicia of the infected person identifies one of the first person or the second person, formats a notification message comprising indicia of the encounter; and
        sends the notification message to at least one of the number of external components.

2. The system of claim 1, further comprising:
    an access control system; and
    wherein the access control systems, upon receiving the notification message, prevents access of at least one of the first person or the second person from an area controlled by the access control system.

3. The system of claim 1, further comprising:
    an access control system; and
    wherein the access control systems, upon receiving the notification message, prevents access of a third person, different from the first person and the second person, from accessing an area previously accessed by at least one of the first person or the second person that is controlled by the access control system.

4. The system of claim 1, wherein the identification of the encounter further comprises the processor performing:
    determining a location of the pressure sensing mat at a first time the second person was proximate to the pressure sensing mat;
    determining the first person was utilizing the pressure sensing mat at a second time; and
    determining the difference between the first time and the second time is less than a transmission viability period of the contagion.

5. The system of claim 1, wherein:
    the number of external components comprise a communication device carried by the second person; and
    wherein the processor determines the second person was proximate to the pressure sensing mat in accordance with a radio frequency communication between the communication interface and the communication device carried by the second person.

6. The system of claim 1, wherein:
    the number of external components comprise a communication device carried by the first person; and
    wherein the processor determines the identity of the first person from a pairing operation performed with the pressure sensing mat and the communication device carried by the first person; and
    wherein the pairing operation comprises at least one of a radio frequency paring or a signal provided by the communication device carried by the first person to the communication interface, wherein the signal comprises indicia of an optical code captured by a camera of the communication device carried by the first person; and
    wherein the notification message comprises indicia of the first person as identified.

7. The system of claim 1, further comprising:
    a data storage comprising biometric data of at least the first person; and
    wherein the processor determines the identity of the first person upon matching a biometric signature comprising biometric data received from the plurality of sensing portions to a record in the data storage associated with the first person.

8. The system of claim 1, further comprising:
    the processor determining whether the pressure sensing mat, at the time of the encounter, was utilized by the first person standing or by the first person seated;
    wherein the transmission range of the contagion comprises a standing transmission range, utilized when the determined use is standing; and
    wherein the transmission range of the contagion comprises a seated transmission range, utilized when the determined use is seated.

9. The system of claim 1, further comprising:
    the processor determining whether the pressure sensing mat, at the time of the encounter, was utilized intermittently by the first person being alternatingly present and absent from the pressure sensing mat; and
    wherein the transmission range of the contagion comprises a transient transmission range, utilized when the determined use is intermittent.

10. The system of claim 1, wherein:
    the encounter comprises a first time period of utilization of the pressure sensing mat by the first person;
    the encounter comprises a second time period of utilization of the pressure sensing mat by the second person; and
    wherein determining that the indicia of the infected person identifies the one of the first person or the second person, having the earlier of the first time period or the second time period, causes the processor to format the notification message comprising indicia of the encounter identifying the one of the first person or the second person, having the later of the first time period or the second time period.

11. A method, for responding to a potential contagion transmission, comprising:
- identifying a first person having used a pressure sensing mat, the pressure sensing mat comprising a plurality of sensing portions;
- identifying an encounter between a second person and the first person having a distance therebetween that is less than a transmission range of a contagion;
- receiving indicia of an infected person;
- upon determining that the indicia of the infected person identifies one of the first person or the second person, formatting a notification message comprising indicia of the encounter; and
- sending the notification message to at least one of a number of external components.

12. The method of claim 11, wherein the identification of the encounter further comprises:
- determining a location of the pressure sensing mat at a first time the second person was proximate to the pressure sensing mat;
- determining the first person was utilizing the pressure sensing mat at a second time; and
- determining the difference between the first time and the second time is less than a transmission viability period of the contagion.

13. The method of claim 11, wherein:
- the number of external components comprise a communication device carried by the second person; and
- determining the second person was proximate to the pressure sensing mat in accordance with a radio frequency communication occurring between a communication interface and the communication device carried by the second person.

14. The method of claim 11, wherein:
- determining the identity of the first person from a pairing operation performed with the pressure sensing mat and a communication device carried by the first person; and
- wherein the pairing operation comprises at least one of a radio frequency paring or a signal provided by the communication device carried by the first person to the communication interface, wherein the signal comprises indicia of an optical code captured by a camera of the communication device carried by the first person; and
- wherein the notification message comprises indicia of the first person as identified.

15. The method of claim 11, further comprising:
- a data storage comprising biometric data of at least the first person; and
- wherein the processor determines the identity of the first person upon matching a biometric signature comprising biometric data received from the plurality of sensing portions to a record in the data storage associated with the first person.

16. The method of claim 11, further comprising:
- determining whether the pressure sensing mat, at the time of the encounter, was utilized by the first person standing or by the first person seated;
- wherein the transmission range of the contagion comprises a standing transmission range, utilized when the determined use is standing; and
- wherein the transmission range of the contagion comprises a seated transmission range, utilized when the determined use is seated.

17. The method of claim 11, further comprising:
- determining whether the pressure sensing mat, at the time of the encounter, was utilized intermittently by the first person being alternatingly present and absent from the pressure sensing mat; and
- wherein the transmission range of the contagion comprises a transient transmission range, utilized when the determined use is intermittent.

18. A mat, comprising:
- a plurality of sensing portions;
- a processor receiving signals from the plurality of sensing portions;
- a communication interface facilitating communications between the processor and a number of external components; and
- wherein the processor:
  - identifies a first person having used the pressure sensing mat;
  - identifies an encounter between a second person and the first person having a distance therebetween that is less than a transmission range of a contagion;
  - receives indicia of an infected person;
  - upon determining that the indicia of the infected person identifies one of the first person or the second person, formats a notification message comprising indicia of the encounter; and
  - sends the notification message to at least one of the number of external components.

19. The mat of claim 18, comprising:
- a data storage comprising biometric data of at least the first person; and
- wherein the processor determines the identity of the first person upon matching a biometric signature comprising biometric data received from the plurality of sensing portions to a record in the data storage associated with the first person.

20. The mat of claim 18, wherein the processor determines the second person was proximate to the pressure sensing mat in accordance with a radio frequency communication between the mat and a communication device carried by the second person.

* * * * *